US 11,445,896 B2

(12) United States Patent
Nadiv et al.

(10) Patent No.: US 11,445,896 B2
(45) Date of Patent: Sep. 20, 2022

(54) METHODS AND SYSTEMS FOR CONTROLLING IMAGES CAPTURING AND TRANSMISSION RATE IN AN IN-VIVO DEVICE

(71) Applicant: Given Imaging Ltd., Yoqneam (IL)

(72) Inventors: Ron Nadiv, Hod-Hasharon (IL); Ori Hay, Haifa (IL); Moran Horesh, Nahalal (IL); Dori Peleg, Haifa (IL); Stas Rozenfeld, Hod Hasharon (IL)

(73) Assignee: Given Imaging Ltd., Yoqneam (IL)

( * ) Notice: Subject to any disclaimer, the term of this patent is extended or adjusted under 35 U.S.C. 154(b) by 976 days.

(21) Appl. No.: 16/073,125

(22) PCT Filed: Jan. 24, 2017

(86) PCT No.: PCT/IL2017/050092
§ 371 (c)(1),
(2) Date: Jul. 26, 2018

(87) PCT Pub. No.: WO2017/130193
PCT Pub. Date: Aug. 3, 2017

(65) Prior Publication Data
US 2019/0029504 A1     Jan. 31, 2019

Related U.S. Application Data

(60) Provisional application No. 62/431,915, filed on Dec. 9, 2016, provisional application No. 62/288,021, filed on Jan. 28, 2016.

(51) Int. Cl.
*A61B 1/045*     (2006.01)
*A61B 1/00*     (2006.01)
(Continued)

(52) U.S. Cl.
CPC .......... *A61B 1/045* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS 8,328,713 B2   12/2012   Ishihara
2007/0244395 A1*   10/2007   Wang ................... A61B 6/5247
                                                                  600/476
(Continued)

OTHER PUBLICATIONS

Ren, et al., "Learning a Classification Model for Segmentation", IEEE International Conference on Computer Vision, 2003, pp. 1-8.
(Continued)

*Primary Examiner* — Jay B Shah

(57) ABSTRACT

Methods for capturing and transmitting images by an in-vivo device comprise operating a pixel array in a superpixel readout mode to capture probe image, for example, according to a time interval. Concurrently to capturing of each probe image, the probe image is evaluated alone or in conjunction with other probe image(s), and if it is determined that no event of interest is detected by the last probe image, or by the last few probe images, the pixel array is operated in the superpixel readout mode and a subsequent probe image is captured. However, if it is determined that the last probe image, or the last few probe images, detected an event of interest, the pixel array is operated in a single pixel readout mode and a single normal image, or a series of normal image, is captured and transmitted, for example, to an external receiver.

9 Claims, 11 Drawing Sheets

(51) Int. Cl.
   *A61B 1/04* (2006.01)
   *G06T 7/246* (2017.01)
   *A61B 5/01* (2006.01)
   *A61B 5/03* (2006.01)
   *A61B 5/07* (2006.01)
   *A61B 5/145* (2006.01)
   *A61B 5/00* (2006.01)
   *G06T 7/00* (2017.01)
   *H04N 5/343* (2011.01)
   *H04N 5/345* (2011.01)
   *H04N 5/347* (2011.01)
   *H04N 5/369* (2011.01)
   *G06T 7/73* (2017.01)

(52) U.S. Cl.
   CPC ...... *A61B 1/00016* (2013.01); *A61B 1/00032* (2013.01); *A61B 1/00036* (2013.01); *A61B 1/041* (2013.01); *A61B 5/01* (2013.01); *A61B 5/036* (2013.01); *A61B 5/073* (2013.01); *A61B 5/14539* (2013.01); *A61B 5/6861* (2013.01); *G06T 7/0014* (2013.01); *G06T 7/246* (2017.01); *H04N 5/343* (2013.01); *H04N 5/345* (2013.01); *H04N 5/347* (2013.01); *H04N 5/3698* (2013.01); *A61B 1/00025* (2013.01); *A61B 5/14503* (2013.01); *A61B 2560/0209* (2013.01); *A61B 2560/0462* (2013.01); *G06T 7/73* (2017.01); *G06T 2207/10068* (2013.01); *G06T 2207/30092* (2013.01); *G06T 2207/30168* (2013.01)

(56) References Cited

U.S. PATENT DOCUMENTS

| | | |
|---|---|---|
| 2008/0170846 A1 | 7/2008 | Wang |
| 2009/0192348 A1 | 7/2009 | Nishino |
| 2009/0299140 A1* | 12/2009 | Wang .................... H04N 7/185 600/118 |
| 2010/0010300 A1* | 1/2010 | Gilad .................... A61B 1/041 600/109 |
| 2010/0016673 A1 | 1/2010 | Bandy et al. |
| 2010/0182412 A1* | 7/2010 | Taniguchi ............. G16H 40/63 348/65 |
| 2010/0220180 A1 | 9/2010 | Lee et al. |

OTHER PUBLICATIONS

Felzenszwalb, et al., "Efficiently Computing a Good Segmentation", Computer Science Department; Cornell University, 1998, pp. 1-8.
Comaniciu et al., "Mean Shift: A Robust Approach Toward Feature Space Analysis", IEEE Transactions on Pattern Analysis and Machine Intelligence, vol. 24, No. 5, May 2002, pp. 603-619.
Liu et al., "Entropy Rate Superpixel Segmentation", IEEE Computer Vision & Pattern Recognition, 2011, pp. 2097-2104.
Vedaldi, et al., "Quick Shift and Kernel Methods for Mode Seeking", European Conference on Computer Vision, 2008, pp. 1-14.
Meyer, "Color Image Segmentation", International Conference on Image Processing, 1992, pp. 303-306.
Levinshtein et al., "TurboPixels: Fast Superpixels Using Geometric Flows", IEEE Transactions on Pattern Analysis and Machine Intelligence, vol. 31, No. 12, Dec. 2009, pp. 2290-2297.
Peer Neubert and Peter Protzel, "Superpixel Benchmark and Comparison," Chemnitz University of Technology, Department of Electrical Engineering and Information Technology, (pp. 1-12).

* cited by examiner

METHODS AND SYSTEMS FOR CONTROLLING IMAGES CAPTURING AND TRANSMISSION RATE IN AN IN-VIVO DEVICE

CROSS-REFERENCE TO RELATED APPLICATIONS

This application is a National Phase Application of PCT International Application No. PCT/IL2017/050092, International Filing Date Jan. 24, 2017, claiming benefit from U.S. Provisional Patent Application(s) Nos. 62/431,915, filed Dec. 9, 2016, and 62/288,021, filed Jan. 28, 2016, all of which are hereby incorporated by reference.

FIELD OF THE INVENTION

The present invention relates to transmission of images from the gastrointestinal ("GI") tract in general, and to controlling of images transmission rate in particular.

BACKGROUND

There are swallowable in-vivo devices which are provided with various types of sensors (e.g., image sensor (imager), pressure sensors, etc.) to take images and measure various parameters within the gastrointestinal ("GI") tract. Such devices are also designed to transmit images (and/or measurement information) in the form of image frames. Swallowable in-vivo devices typically include non-rechargeable one or more batteries. Since transmission of each image frame from an in-vivo imaging device to an external receiver consumes battery energy, and in-vivo imaging devices are typically required to transmit a large number of images (e.g., in the order of tens of thousands) of the GI tract, battery power 'housekeeping' is of concern.

Since transmission of image frames from in-vivo devices is known as a major power consumer, where every single data bit requires battery energy for its transmission, significantly reducing the number of data bits that actually transmitted would conserve a lot of battery power. One solution that mitigates the problem associated with battery power consumption is using an adaptive frame rate ("AFR") technique, which involves, in general, using two distinct frame transmission rates ("FTRs"): one that is relatively low (e.g., 4 frames per second ("FPS")), to reduce the number of image frames transmitted, and another that is relatively high (e.g., 24 FPS). The lower FTR is used every time the in-vivo device is estimated (e.g., based on motion detection) to be stationary in the GI tract (and therefore its imager captures redundant images that need not be transmitted, which saves battery energy). The higher FTR is used in order not to avoid skipping GI sites of interest when the in-vivo device is moving in the GI tract. However, using two, fixed, FTRs still have drawbacks. For example, the in-vivo device still wastes battery energy to produce and transmit redundant images when the in-vivo device is stationary, though at lower numbers at lower FTR. In addition, the response time of the in-vivo device to transition between FTRs primarily depends on the FTRs themselves, which is more of a problem for the lower FTR.

In addition, the information that an external receiver uses to determine whether the in-vivo device is stationary or not is included in the transmitted data frames and responded to by the external receiver. Therefore, when the in-vivo device operates in the low FTR, it may take the in-vivo device a considerable amount of time (a whole, relatively long, work cycle) to transmit that information to the receiver. Consequently, it may take the receiver a relatively long time (e.g., in the order of tens, and even hundreds, of milliseconds) to determine, based on that information, whether the in-vivo device should transition from the low FTR to the high FTR, and by the time the FTR transition actually occurs, important GI sites might be skipped.

SUMMARY

It would, therefore, be beneficial (for example, in terms of saving battery power and number of images that a user may need to view for analysis) to have a swallowable in-vivo device that can determine when it should capture and transmit an image and when it should refrain from doing so. It would also be beneficial (for example, in terms of imaging coverage of the GI tract) to have a swallowable in-vivo device that is fast to respond when it should capture and transmit an image. It would also be beneficial to have an in-vivo device that is capable of detecting its relative movement very fast, and, while monitoring its relative movement, is capable of using low battery power when it is stationary, or whenever capturing and transmission of image frames is unjustified clinically, and increasing its image frame transmission rate every time it moves, or every time new image frames are worth transmitting.

While using different FTRs is beneficial in saving battery power in an in-vivo device, it would be beneficial to have a FTRs mechanism redesigned in a way that it would allow the in-vivo device to use the battery power more efficiently during a medical procedure, and to respond quickly to movement of the in-vivo device in the GI tract, or to any change in a scene or in a scenery in the GI tract, irrespective of the rate at which images are transmitted.

An embodiment includes a method for capturing and transmitting images from the gastrointestinal (GI) tract by an in-vivo device including, by an in-vivo device, autonomously moving in the GI tract, the in-vivo device comprising an imager comprising an image pixel array ('pixel array' for short), and an illumination source, the pixel array operable in a superpixel readout mode of operation in which designated superpixels in the pixel array capture regular probe images by reading clusters (subgroups) of pixels that respectively collectively form larger pixels, and in a single pixel readout mode of operation in which the pixel array captures normal images by reading all or some of the pixels individually (e.g., each pixel is read individually), performing, operating the pixel array in the superpixel readout mode according to a time interval (e.g., according to a schedule) to capture a series of regular probe images P1, P2, P3, . . . , Pn;
  for each regular probe image Pi (i>1) that is captured at time t, performing:
    (i) comparing the regular probe image Pi with one or more past regular probe images; and
    (ii) determining, based on the comparison result, whether to capture a normal image;
    (iii) if a normal image is to be captured, operating the pixel array in the single pixel readout mode to capture a normal image, and transmitting the normal image before capturing a next regular probe image Pi+1; and
    (iv) if no normal image is to be captured, operating the pixel array in the superpixel readout mode to capture a next regular probe image Pi+1.

The comparison result may be or include detection of movement of the in-vivo device relative to a scene or scenery imaged by the pixel array, or detection of a change in the scene or scenery.

Comparing the regular probe image Pi with the past regular probe images may include comparing a picture or image parameter or feature in, related to or derived from the regular probe images. The pixel array may be operated in the single pixel readout mode when the compared picture or image parameter or feature indicates, for example, past or current movement of the in-vivo device.

An embodiment may include selecting the superpixel configuration according to the type of the picture or image parameter or feature in, related to or derived from one or more past (previously captured) regular probe images, or from a normal image. A superpixel configuration may be selected for the superpixel readout mode according to an indicated event of interest. An embodiment may include measuring a physiological parameter to corroborate or confirm an indication that the in-vivo device is moving. The method may include detecting content or bubble in the GI tract and determining whether this indicates that the in-vivo device is moving, or that the scene is moving (relative to the in-vivo device) or that the scene or scenery has changed, rather than the content or bubble is moving. A change from a scene or scenery with content to a scene or scenery without content while the capsule stands still (as can be sensed by, for example, a movement detector or by a second pixel array) may trigger or cause the capturing and transmission of a normal image, or of a series of normal images.

The illumination source of the in-vivo device may be operated in a first illumination mode (e.g., a power saving mode) when the image is operated in the superpixel readout mode, and in a second illumination mode (e.g., an optimal illumination mode) when the image is operated in the single pixel readout mode.

An embodiment may include capturing a conditional probe image between two successive regular probe images, comparing the conditional probe image with one or more past regular probe images and/or with one or more past conditional probe images and/or with one or more normal images. A 'conditional probe image' may include a probe image that is captured during a time period that is initially allocated for capturing and transmitting a normal image but, ultimately, a decision is made (e.g., by a controller) not to capture and transmit a normal image during that time. A conditional probe image may be a probe image similar to regular probe image except that a conditional probe image is a probe image that may be captured between two successive, or 'adjacent', regular probe images if a decision is made, e.g., by a controller, that no normal image is to be captured and transmitted between the two successive regular probe images. A past conditional image may refer to a conditional image that is ultimately captured and thus exists and can be compared to other images.

Determining whether or not to capture a normal image may include predicting movement of the in-vivo device based on previous comparison results and/or previous indications regarding, for example, an anatomical region in which the in-vivo device currently resides in.

Detection of any pathologically abnormal tissue, or, in general, detection of any event of interest in one or more regular probe images may trigger the capturing and transmission of one normal image, or, in some embodiments, a series (a burst) of (e.g., predetermined number of) normal images. For example, detection of a pathology (e.g., a polyp candidate, an ulcer, etc.) or a landmark (e.g., ileocecal valve (ICV) or the colon flexures) in at least one regular probe image, or detection of entrance or exit to, or from, a specific segment of the GI tract, or detection of an organ of the GI tract (e.g., stomach, colon) may be regarded as events of interest triggering the capturing and transmission of a normal image or a series (a burst) of normal images. (An 'event of interest', as used herein, refers to an imaged object or image detected, by one or more probe images (regular probe images and/or conditional probe images) and/or normal images, that may include or be landmark in the GI tract, location in the GI tract, segment of the GI tract, organ of the GI tract, a particular pathology (e.g., polyp, ulcer, diverticulum, Crohn' disease, bleeding, etc.) (Other or additional pathologies, locations/sites in the GI tract and GI organs can be regarded as 'events of interest' triggering the capturing and transmission of a normal image or a series (a burst) of normal images.)

In some embodiments, a score is calculated for each regular probe image, for example based on imaging parameter(s) and/or feature(s) that are computer-detectable in the images, and score values may be used individually or jointly in determining a capturing and transmission of a particular image. (A last calculated score may be used individually or in conjunction with one or more scores that were calculated for past probe images.) An embodiment for capturing and transmitting images by an in-vivo device swallowed by a subject may include performing, by a controller included in the in-vivo device, the in-vivo device including an imaging pixel array operable in a superpixel readout mode of operation in which the pixel array captures regular probe images by reading clusters of pixels (e.g., a portion, or portions, of the pixel array), and in a single pixel readout mode of operation in which the pixel array captures normal images by reading its pixels individually: (i) operating the pixel array in the superpixel readout mode to capture a regular probe image, and calculating a score for the regular probe image; (ii) if the score of the regular probe image is not a triggering score (e.g., if the value of the score is less than a threshold value), operating the pixel array in the superpixel readout mode and capturing a subsequent regular probe image, and calculating a score for the subsequent regular probe image, and if the score of the subsequent regular probe image is also not a triggering score (e.g., if the value of this score is also less than the threshold value), calculating a difference score representing a difference between the two scores or difference(s) between the regular probe image and the subsequent regular probe image, and if the difference score is also not a triggering difference score (e.g., if the value of the difference score is less than another threshold value), repeating steps (i)-(ii); and (iii) if one of the score of the regular probe image, the score of the subsequent regular probe image and the difference score is a triggering score (e.g., if the value of a score is equal to or greater than the respective threshold value), capturing and transmitting a normal image or a series of normal images by operating the pixels in the single pixel readout mode, and repeating steps (i)-(iii).

Also provided is a swallowable in-vivo device that includes a pixel array, an illumination source and a controller. The controller may be configured to operate the pixel array and the illumination source in accordance with the methods described herein. The swallowable in-vivo device may also include a sensor in addition to the imaging sensor (pixel array) for sensing a non-image parameter of the GI tract, or to sense a physiological parameter related to the subject swallowing the in-vivo device, or to sense a parameter related to movement of the in-vivo device. The second sensor may be selected from a group of sensors consisting of: a pH sensor, a pressure sensor, a temperature sensor, an accelerometer, a motion sensor, a magnetometer, a magnetic field sensor and a second pixel array. A sensed non-image parameter may be used to corroborate or refute a determination made by using a probe image, or probe images, that a normal image, or a series of normal images should be captured and transmitted.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION OF THE INVENTION

Figure 1A:
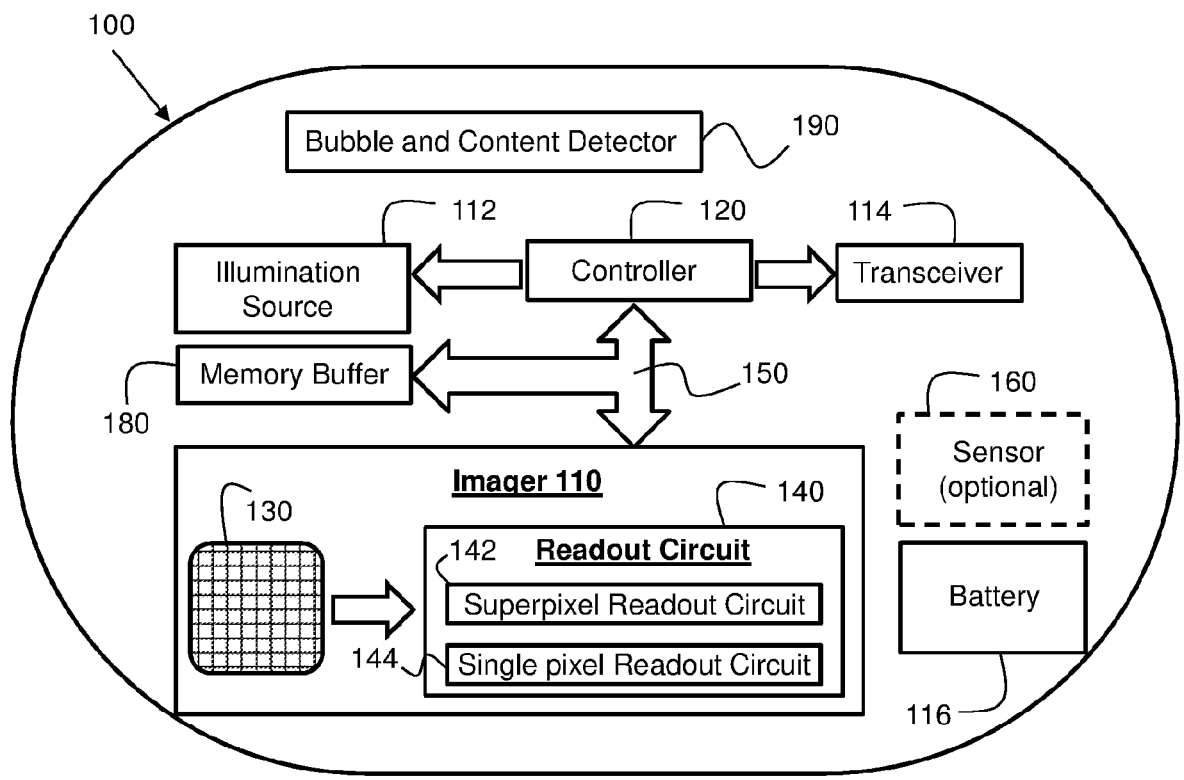
FIG. 1A shows a block diagram of an in-vivo device according to an example embodiment of the invention.

The description that follows provides various details of exemplary embodiments. However, this description is not intended to limit the scope of the claims but instead to explain various principles of the invention and the manner of practicing it.

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

In-vivo imaging devices transmit images to an external receiver using image frames, where each image frame includes data representative of an image captured in vivo by the in-vivo device, and, optionally, data representative of a physiological parameter (e.g., pH, pressure, temperature), or non-imaging parameter, that the in-vivo device may sense by using an on-board sensor. As described below, an image that is captured in order for it to be transmitted may be first stored in a memory buffer, and, when conditions permit, a series of images, which are stored in the memory buffer, may be transmitted in one transmission 'burst'. Therefore, one 'image frame' may, according to the present invention, include multiple images, rather than using the 'one image per frame' method.

Transmitting data is power consuming, so, to conserve battery energy, it would be beneficial to refrain from transmitting any data when the in-vivo device is stationary (and probably 'sees' the same scene), and also whenever the in-vivo device is moving but there is nothing interesting to transmit to an external receiver.

Superpixel image segmentation techniques have been known to be useful for segmenting digitized images into discrete pixel clusters to enhance image analysis. A discrete, or separate, pixel cluster, called superpixel, represents, is or consists of, adjacent image pixels that have similar characteristics, such as color, texture, intensity, etc. Various algorithms for superpixel segmentations have been proposed, for example the ones described in "Learning a classification model for segmentation," (X. Ren and J. Malik, in ICCV, 2003); "Efficiently computing a good segmentation," (P. F. Felzenszwalb and D. P. Huttenlocher, 1998); "Mean shift: A robust approach toward feature space analysis," (D. Comaniciu and P. Meer, TPAMI, vol. 24, 2002); "Entropy rate superpixel segmentation." (M.-Y. Liu, O. Tuzell, S. Ramalingam, and R. Chellappa, in CVPR, 2011); "Quick shift and kernel methods for mode seeking," (A. Vedaldi and S. Soatto, in ECCV, 2008); "Color image segmentation," (F. Meyer, in ICIP92, 1992); and in "Turbo pixels: Fast superpixels using geometric rows," (A. Levinshtein, A. Stere, K. Kutulakos, D. Fleet, S. Dickinson, and K. Siddiqi, TPAMI, 2009). (Information collected from the article "Superpixel Benchmark and Comparison"; by Peer Neubert and Peter Protzel; Chemnitz University of Technology, Department of Electrical Engineering and Information Technology).

Different superpixel configurations (and associated algorithms) generally involve defining and reading out different clusters of pixels, rather than reading out individual pixels, and are commonly known in the field of digital imaging as "binning". Embodiments of the present invention may use one or more binning configurations (that are also referred to here as 'superpixel configurations') for monitoring the in-vivo device's movement in the GI tract, or to see if there is a change in the scene or scenery imaged by the in-vivo device that justifies capturing and transmitting a normal image, and significant reduction in the power consumption of the device's battery.

The description herein mentions movement of the in-vivo device in general. However, 'movement' also refers, among other things, to a change in a scene or scenery that the in-vivo device 'sees' (that is imaged by the pixel array) and justifies capturing and transmission of a normal image or a series of normal images. For example, the in-vivo device may be stationary while the GI intestines themselves may move (e.g., contract and distend), thus the imaged scene or scenery, by revealing a new scene or scenery to the in-vivo device, may justify the capturing and transmission of a normal image (or a series of normal images).

Regardless of the superpixel scheme used, using superpixels speeds up image processing because each superpixel is processed as a whole, rather than having to process separate (and many) pixels individually, and the number of superpixels is by far smaller than the number of individual pixels. For the sake of simplicity and convenience, the description below refers to 'superpixels' as means for only capturing (but not transmitting) regular probe images and, in some embodiments, also conditional probe images. However, the present invention is not limited in this regard, as superpixels may, in some embodiments, also be used to capture and transmit normal images.

FIG. 1A shows a block diagram of a swallowable in-vivo device 100 according to an example embodiment of the invention. In-vivo device (e.g., capsule type) 100 may include an imager 110 and a controller 120. Imager 110 may include an image sensor, for example a pixel array that is schematically shown at 130 (e.g., a pixel array may include, or be, a matrix of 256×256 pixels), and a pixel readout circuit 140 for reading, by controller 120, via a readout bus 150, the analog signals output by pixel array 130. In-vivo device 100 may also include an illumination source 112 (for example light emitting diodes—'LEDs') for illuminating a site for pixel array 130, and a battery 116 for powering up in-vivo device 100.

Pixel readout circuit 140 may include a superpixel readout circuit 142 and a single pixel readout circuit 144. Superpixel readout circuit 142 may output, for controller 120 to read, superpixel signals such that each superpixel signal represents a number of pixel analog outputs of a cluster of adjacent pixels in pixel array 130. Single pixel readout circuit 144 may output, for controller 120 to read, single pixel signals such that each single pixel signal represents a pixel output of a single pixel in pixel array 130.

Controller 120 may controllably operate imager 110 in a superpixel readout mode of operation in which imager 110 captures images by the readout circuit 140 grouping, or clustering, adjacent pixels in the pixel array to superpixels, and reading each particular superpixel cluster en masse; that is, by reading one superpixel signal that represents the entire cluster of adjacent pixels of the particular superpixel. An image that is captured by using the superpixel mode of operation is referred to herein as a 'probe image'.

Controller 120 may controllably operate imager 110 in a single pixel readout mode of operation in which imager 110 (that is, pixel array 130) captures images by the readout circuit 140 reading each pixel of the pixel array individually (rather than collectively, as for a superpixel). An image that is captured by using the single pixel mode of operation is referred to herein as a 'normal image'. If controller 120 determines to apply the superpixel readout mode, it may send (150) a binning (superpixel) control signal to readout circuit 140, instructing readout circuit 140 to select a particular binning (superpixel) configuration for use. Controller 120 may select a superpixel configuration according to an indicated event of interest. For example, controller 120 may select a relatively 'sparse' superpixel configuration when in-vivo device 100 is in a particular site in the GI tract, and a denser superpixel configuration when in-vivo device 100 is in another site in the GI tract. Controller 120 may apply (to imager 110) one, predetermined, binning configuration, or a binning configuration that is selectable from two or more such schemes. Readout circuit 140 may control the way superpixel readout circuit 142 operates according to the controller's binning selection instruction, such that pixels in pixel array 130 are clustered to form superpixels in accordance with the controller's selected binning configuration. Controller 120 may select a binning configuration according to, adapted to or suitable or optimized for, the picture or image parameter or feature of or in the image that may be used, for example, for comparing probe images, or according to the purpose of the probe images comparison process. For example, if the purpose of the comparison is detecting movement of in-vivo device 100, controller 120 may use a binning configuration that enhances, or is optimized for, movement detection, for example in terms of detection speed, sensitivity and accuracy. Selecting a binning/superpixel configuration means selecting a particular superpixel segmentation algorithm that sets the pixels' format of the superpixels and the way the values of the formatted superpixels are read out. In another example, if the purpose of the comparison is detecting polyps in the GI tract, controller 120 may use a binning configuration that is more suitable (e.g., optimized) for detecting rounded objects.

Controller 120 is configured to select (for example according to (e.g., once per) a predetermined time interval, or once per a fixed or preselected, or according to circumstances; e.g., whenever required) a mode of operation for imager 110 from the superpixel readout mode and single pixel readout mode. In one example, controller 120 may be configured to operate the imager in the superpixel readout mode according to a predetermined (probing) time interval (e.g., once per a predetermined or fixed time period) to capture a series of probe images P1, P2, P3, . . . , Pn, and while the probe images P1, P2, P3, . . . , Pn are captured, one probe image at a time, controller 120, starting from a selected probe image Pi (i>1), may compare probe image Pi with one or more past probe images ('past probe image' is any probe image that temporally precedes probe image Pi; images are typically ordered in an image stream by a capture time, but other methods of determining a preceding or past image may be used), and determine, based on the comparison result, whether it should operate imager 110 in the single pixel readout mode to capture, and subsequently transmit, a normal image before a next probe image Pi+1 is captured. Controller 120 may determine whether to capture all or particular normal images by predicting movement of the in-vivo device from previous comparison results and/or from indications regarding an anatomical region (e.g., stomach, small bowel, colon, etc.) in which the in-vivo device currently resides. (Determining whether to capture a normal image, or a series of normal images, may include predicting movement of in-vivo device 100 based on previously calculated image score and/or difference scores.)

Controller 120, or other processors, may be configured to carry out embodiments of the invention by for example including dedicated circuitry or executing software or code stored for example in a memory.

Comparing probe image Pi with the one or more past (preceding) probe images by controller 120 may include comparing an image parameter or an image feature related to, found in or derived from the probe images. An image parameter or feature in an image may characterize, or indicate, the in-vivo device's spatial orientation and/or whereabouts in the GI system at the time the probe image is captured. An image parameter that controller 120 may use in the probe image comparison process may be any imaging, or imager, operational parameter related to, for example, the operation of imager 110, for example light intensity, light amplifier gain, a particular color, light exposure time, etc. An image feature that controller 120 may use in the probe image comparison process may be any feature that, for example, can be, or is, visually or computationally (or otherwise) conspicuous in the images subject of the comparison, for example it may be a line (e.g., representing a tissue fold line, a wrinkle line, etc.), an object (e.g., polyp), a shadow (e.g., between tissue folds) or a line(s) pattern that can be detected in the images being compared. Controller 120 may use such parameters and features as a reference to (e.g., based on which controller 120 can) determine or estimate movement and/or speed and/or any other physical condition or state of in-vivo device 100. Controller 120 may operate imager 110 in the single pixel readout mode every time controller 120 determines that the compared picture parameter or feature related to, found in or derived from the probe images indicates that in-vivo device 100 is moving or has moved. As used throughout the description, the phrase "indication that a device is moving, or has moved" may means "indication that the in-vivo device is moving relative to a scene or scenery that is captured, or imaged, by imager 110, or indication that the scene or scenery, as captured by the imager, is changing or has changed".

In-vivo device 100 may include one or more additional sensors; e.g., sensor(s) 160, to sense or measure, for example, a non-image parameter (e.g., physiological parameter related to the subject swallowing in-vivo device 100; e.g., non-image parameter of the GI tract), or, for example, a parameter related to the condition or state of the in-vivo device. The non-image parameter may be any parameter selected from the group consisting of: movement of the in-vivo device, acceleration of the in-vivo device, pH, pressure and temperature (to mention a few parameters). An imaging parameter (as opposed to an image parameter which is a parameter identifiable or detectable in images), for example, an imaging amplifier gain and an imaging light exposure time, may be used to compare between images, for example by calculating a score for each image and using the scores in the comparison process. Sensor 160 may include one or more sensors. For example, sensor 160 may include an accelerometer sensor to sense movement of the in-vivo device, and a pH sensor to sense the location of the in-vivo device in the GI tract.

Controller 120 may use output signal(s) of sensor 160 to corroborate or confirm, or refute, the determination that the compared image parameter or feature related to, found in or derived from the compared probe images indicates that in-vivo device 100 is moving or has moved. For example, if a comparison of probe images indicates that in-vivo device 100 is moving, but a pressure measurement measured by sensor 160 indicates that it is not moving, or vice versa, controller 120 may determine that in-vivo device 100 is not moving. That is, controller 120 may determine that in-vivo device 100 is, indeed, moving or has moved based on the two example indications. For example, controller 120 may determine that in-vivo device 100 is moving or has moved only if both instances (the probe images comparison result and the sensor readings) simultaneously indicate that in-vivo device 100 is moving or has moved. Only then controller 120 may operate imager 110 in the single pixel mode and transmit a normal image or a series of normal images. Otherwise (e.g., movement of in-vivo device 100 is refuted or inconclusive), controller 120 may operate imager 110 in the superpixel readout mode and capture another regular probe image.

Sensor 160 may be or may include a device (e.g., sensor, detector or transducer) that can directly indicate movement of in-vivo device 100. For example, sensor 160 may be or may include an accelerometer (e.g., one-, two- or three-dimensional accelerometer), a magnetometer, a magnetic field sensing device, etc. Such a device may be used solely to determine movement of in-vivo device 100, or in conjunction with an image-based movement detection. Such an on-board device may directly sense absolute movement and relative location or orientation of in-vivo device 100, for example relative to an external coordinate system. Using an output signal of such a device (e.g., sensor, detector or transducer) may enable controller 120 to corroborate or refute an initial probe image(s) based determination that in-vivo device 100 moved relative to the GI site the in-vivo device is at, or that a scene has moved relative to the in-vivo device. Sensor 160 may be used to sense a non-image parameter of the GI tract or of the in-vivo device itself, and controller 120 may use the sensory information to corroborate, or refute, an indication that the in-vivo device is moving.

While in-vivo device 100 is in the GI tract it may take pictures of bubbles or content by using bubble and content detector 190 (e.g. implemented by controller 120 such that detector 190 may in some embodiments be controller 120, or may be another unit). ('Content'—stool, feces, excreta, etc. that may be anywhere in the GI tract.) Bubble and content detector 190 may include an algorithm that is designed to detect bubbles, and another algorithm that is designed to detect bubbles. In some embodiments, controller 120 is configured to detect an absolute movement of in-vivo device 100. Controller 120 may use various sensory information to determine whether content or detected bubbles in the GI tract, which are detected by bubbles and content detector 190, move relative to the in-vivo device, or it is the in-vivo device that moves relative to the content or bubbles. If it is the content or bubbles that move relative to the in-vivo device then, controller 120 may negate (refute) other indications (e.g., image-based indication) that in-vivo device 100 is moving or has moved. (The discrepant movement indication is to be temporally adjacent to the movement indication in order to refute the movement indication. That is, if a time difference between a discrepant movement indication and a movement indication is relatively long; e.g., in the order of hundreds of milliseconds, the discrepant movement indication may not refute the movement indication.) In other embodiments, controller 120 is configured to detect relative movement of in-vivo device 100. In these embodiments, controller 120 may determine whether the scene or scenery, as captured by imager 110 (by pixel array 130), is changing or has changed regardless of whether it is/was the content, or bubbles, that is moving or moved, or the in-vivo device.

In some embodiments, a change from a scene or scenery with content (e.g., excretion) or bubbles to a scene or scenery without content or bubbles while the capsule stands still (a condition that can be sensed by, for example, an on-board movement detector (e.g., accelerometer) or by a second pixel array) may trigger capturing and transmission of a normal image, or a series of normal images, by in-vivo device 100.

As described herein, the process of taking probe images is a battery energy saving process, because probe images require less resources (e.g., less illumination, less processing, etc.) than normal images, and, in addition, probe images are not transmitted to an external receiver. To make this process even more frugal in terms of battery energy consumption, probe images may be captured by controller 120 operating illumination source 112 in a first operation mode (e.g., power saving mode), which is an operation mode in which controller 120 may operate illumination source 112 with the lowest light intensity possible that still enables controller 120 to systematically assess probe images individually and to compare between probe images (for example by using the picture or image parameter or feature that is related to, found in or derived from the probe images), for example to detect movement of in-vivo device 100 or changes in a scene or in a scenery, or any event of interest. (Probe images may be used; e.g., compared, for other purposes, for example to detect a polyp or another pathology, or another event of interest, after which controller 120 may increase the normal images capturing and transmission rate, for example progressively or stepwise, at which controller 120 may capture and transmit normal images as controller 120 detects (e.g., by using probe images and maybe other sensory information), for example, movement of in-vivo device 100 or any other event of interest.)

A second battery power mode is a full power mode (or normal power mode, or optimal power mode), which is an operation mode in which controller 120 operates illumination source 112 to provide optimal, or normal, light conditions for capturing normal images as best as possible. Controller 120 may determine to operate illumination source 112 in the power saving mode or in the optimal power mode depending on the type of image that is to be captured—a probe image or a normal image. In-vivo device 100 may include a light control circuit (not shown in FIG. 1A) that controller 120 may use to transition illumination source 112 between the power saving mode and the power normal mode. In-vivo device 100 may also include a transceiver 114 that controller 120 may use to transmit normal images (with or without sensory information that is obtained from sensor 160). (Probe images and conditional probe images are not transmitted by the in-vivo transmitter.) Controller 120 may use transceiver 114 to receive data (e.g., instructions) from an external system, for example to change a mode of operation of, for example, imager 110, illumination source 112, etc., or controller 120 may decide a mode of operation in-situ, based on processing of various 'on-board' sensory information that in-vivo device 110 may collect autonomously.

In-vivo device 100 may include a memory buffer 180, for example, for storing normal images and metadata. Controller 120 may operate pixel array 130 in the single pixel readout mode to capture normal images, and store captured normal image in memory buffer 180. On the one hand, memory buffer 180 is filled by controller 120 with normal images, and, on the other hand, controller 120 may empty memory buffer 180 from normal images by transmitting buffered normal images that are stored in memory buffer 180. Controller 120 may use transceiver 114 to transmit buffered normal images according to a transmission queue, or transmission order, whenever in-vivo device 100 can transmit data. Capturing and transmission of a normal image or a series of normal images may include storing each captured normal image in memory buffer 180 and orderly transmitting stored normal images according to a transmission queue. 'Orderly' may mean transmitting stored normal images according to a time of capture of the normal images, with the first captured normal image being the first to be transmitted, the second captured normal image being the second to be transmitted, and so on. If images are transmitted using a 'one-image-per-one frame' method, then image frames are transmitted according to the capture time of the respective images. If multiple images are transmitted in a frame, the image data within the frame may be arranged according to, e.g., the order of their capture.

Storing normal images in memory buffer 180 is advantageous, for example, in cases where the normal images capturing rate is higher than the maximum images transmission rate. (The capturing rate of probe images is, or can be designed to be, higher; e.g., 64 images per second, than the images transmission rate, and it may occur that, at times, a few successive probe images result in successive normal images. However, since normal images cannot be transmitted as fast, at least some of them may have to be buffered and controllably transmitted whenever possible.)

Figure 1B:
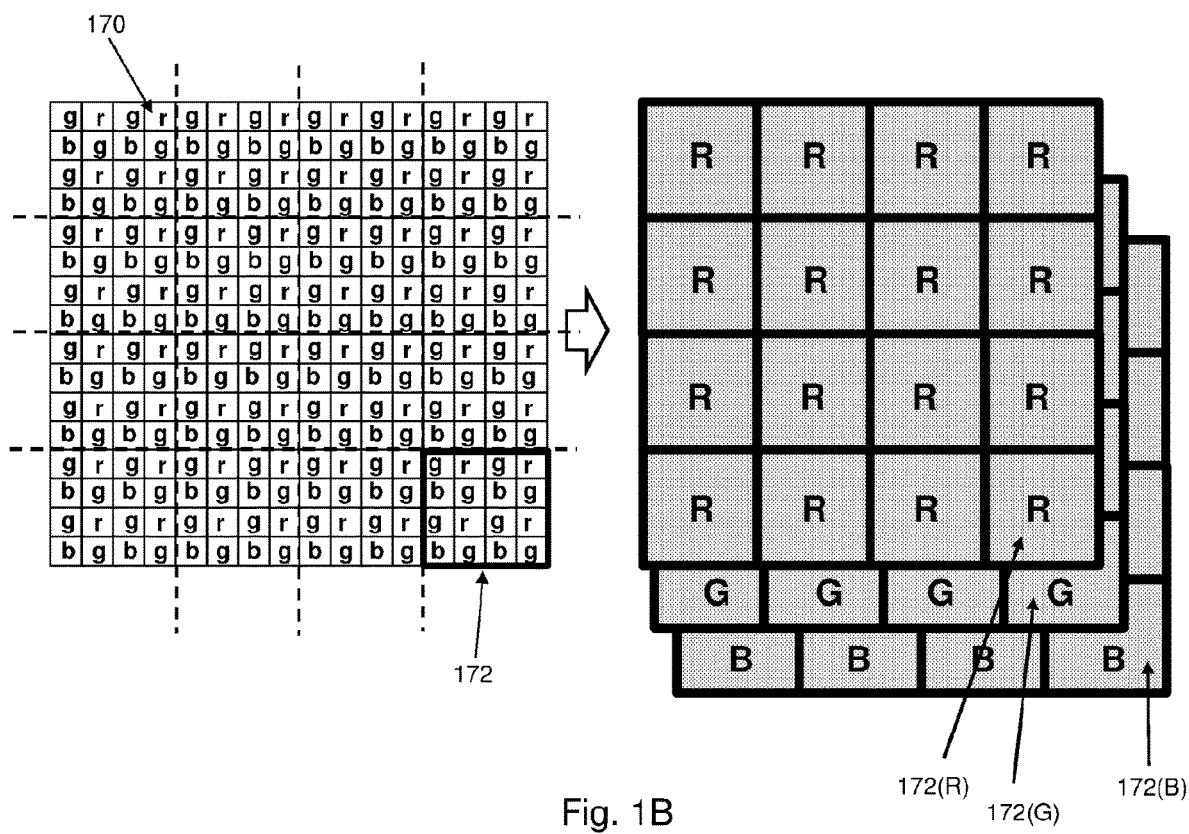
FIG. 1B shows an example way to produce a probe image from a pixel array.

FIG. 1B shows an example way to produce a probe image by using a pixel array 170. Pixel array 170 includes red pixels (designated as 'r' pixels), green pixels (designated as 'g' pixels) and blue pixels (designated as 'b' pixels). In the example of FIG. 1B, pixel array 170 includes a matrix of 16×16 pixels. In the single pixel readout configuration pixels of pixel array 170 are read out individually, thus producing, for example, 256 analog signals. However, pixel array 170 may be partitioned to, for example, 16 (4×4) superpixels, where each superpixel includes a pixel subset, or pixel cluster, that includes 64 'basic' pixels. An example superpixel is shown at 172. Signals that are output from the four red pixels of superpixel 172 may be read as one signal that represents the red color of superpixel 172. (The red color representation of superpixel 172 is shown at 172(R).) Similarly, signals that are output from the eight green pixels of superpixel 172 may be read as one signal that represents the green color of superpixel 172. (The green color representation of superpixel 172 is shown at 172(G).) Similarly, signals that are output from the four blue pixels of superpixel 172 may be read as one signal that represents the blue color of superpixel 172. (The blue color representation of superpixel 172 is shown at 172(B).) The red signal, the blue signal and the green signal of each superpixel may be electrically converted into a color signal that represents the color of the entire superpixel 172. Using this superpixel configuration, the number of signals that represent pixel array 170 can be reduced, for example, from 256 to 16, which is beneficial, for example, in terms of significantly reducing image processing time and power saving. (Other, or several, superpixel configurations may be used, and a particular superpixel configuration may be selected, for example by controller 120, for use at a given time from a group of superpixel configurations according to a predetermined condition that may be related to a landmark in the GI tract, or to a segment or organ of the GI tract, or to a pathology; e.g., polyp, ulcer, diverticulum, Crohn's disease, bleeding, etc.)

Figure 2A:
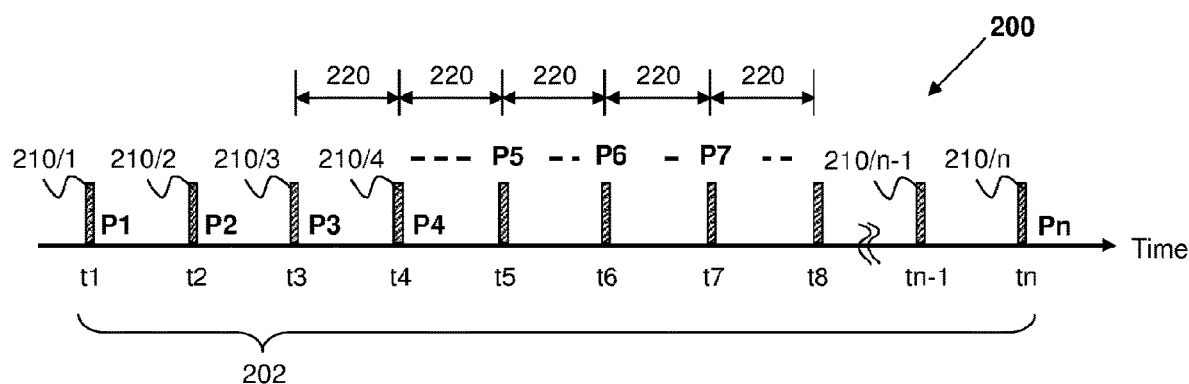
FIG. 2A illustrates a timeline of a series of probe images according to an example embodiment of the invention.

FIG. 2A schematically illustrates a timeline 200 of a series 202 of probe images according to an example embodiment of the invention. FIG. 2A is described in association with FIG. 1A. For the sake of demonstration it is assumed that in-vivo device 100 and the scene or scenery that in-vivo device 100 images, are stationary throughout of image series 202, so that FIG. 2A shows a series of (regular) probe images (image series 202) but not normal images. That is, when in-vivo device 100 is stationary during a clinical procedure, or a series of probe images captured by in-vivo device 100 suggest that the scene is stationary, or the scenery has not changed, this means that there is no reason to capture and transmit a normal (pixel wise 'full-size') image, thus saving processing resources and time, as well as battery power. (The stationary condition of the in-vivo device may be detected 'indirectly', for example by using probe images, or 'directly', for example by using a movement sensor (e.g., an accelerometer), or this condition may be detected by using both probe images and a movement sensor.)

In some embodiments, detection of any pathologically abnormal tissue segment, or, in general, detection (by a controller; e.g., controller 120 of in-vivo device 100) of any event of interest, pathologically or otherwise, in a single regular probe image, or in more than one regular probe images, may trigger (e.g., cause controller 120 to initiate) the capturing and transmission of one normal image, or, in some embodiments, the capturing and transmission of a series (e.g., a predetermined number) of normal images. For example, detection of a potential polyp in at least one regular probe image, or detection of entrance or exit to, or from, a specific segment of the GI tract may cause a controller (e.g., controller 120 of in-vivo device 100) to trigger the capturing and transmission of a normal image, or capturing and transmission of a series of normal images, for example a series of predetermined number of normal images, for example a series of six normal images. The predetermined number of normal images in a series of normal images may depend on, for example, the type of event of interest (e.g., type of pathology or location of the in-vivo device in the GI tract) that is detected by one or more regular probe images.

When in-vivo device 100 is swallowed, controller 120 may initially start operating image 110 in the superpixel readout mode to capture one probe image at a time, starting at time t1 when pixel array 130 captures probe image P1 (shown at 210/1). At time t2, controller 120 operates in-vivo image 110 in the superpixel readout mode again to capture a subsequent (e.g., a second) probe image (probe image P2, as shown at 210/2), according to a time interval 220 (e.g., according to a schedule dictated by, for example, time interval 220). At time t3, controller 120 operates in-vivo image 110 again in the superpixel readout mode to capture a subsequent (third) probe image (probe image P3, as shown at 210/3), and so on.

After controller 120 obtains the second probe image (probe image 210/2) at time t2, controller 120 may compare an image parameter or feature in, related to or derived from probe image 210/2 with a corresponding image parameter or feature in probe image 210/1, for example, to determine whether in-vivo device 100 is moving or has moved. Since in-vivo device 100 is stationary (per the assumption above), control 120 refrains from operating pixel array 130 in the single pixel readout mode; that is, controller 120 refrains from capturing a normal image, and prepares for the subsequent probe image.

Similarly, after controller 120 obtains the third probe image (probe image 210/3), at time t3, controller 120 may compare an image parameter or feature in, related to or derived from probe image 210/3 with a corresponding image parameter or feature in any of the preceding probe images 210/1 and 210/2, or in both probe images, for example, to determine whether in-vivo device 100 is moving or has moved. Since in-vivo device 100 is stationary (per the assumption above), control 120 refrains again from operating pixel array 130 in the single pixel readout mode; that is, controller 120 refrains, again, from capturing a normal image. The same process may be repeated for every probe image in series 202 of probe images. With respect to FIG. 2A, controller 120 may operate illumination source 112 only in the power saving mode, as only probe images are captured. (Per the example described above no normal images are captured in FIG. 2A.)

Controller 120 may initiate capturing of probe images according to (once every) predetermined time interval or time period 220. In some embodiments, controller 120 may operate imager 110 in the superpixel readout mode (and illumination source 112 in the power saving mode) to obtain 64 probe images per second, so that the time interval (220) is 15.625 milliseconds (1/64 second).

Figure 2B:
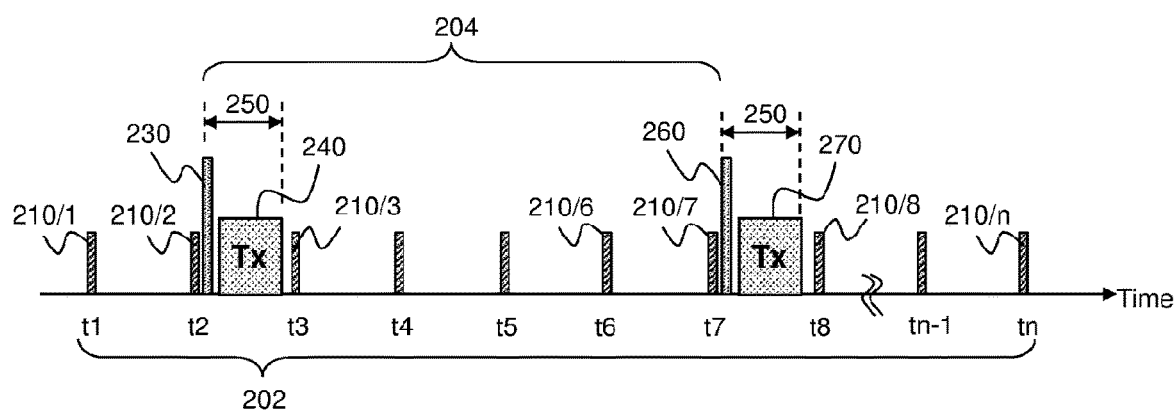
FIG. 2B illustrates the series of probe images of FIG. 2A with example normal images that are interspersed between them according to an example.

FIG. 2B shows the series of probe images 202 of FIG. 2A with two example normal images that are interposed between them. FIG. 2B is described in association with FIG. 2A and FIG. 1A. After controller 120 operates imager 110 at time t2 to capture probe image 210/2 controller may compare probe image 210/2 with probe image 210/1 (for example it may compare a parameter or feature in, related to or derived from them). Assuming that the comparison result indicates to controller 120 that in-vivo device 100 is moving at time t2, or it moved between times t1 and t2, controller 120 operates imager 110 in the single pixel readout mode to capture a normal image 230 before it operates imager 110 again in the superpixel readout mode to capture the next scheduled probe image (probe image 210/3), for example according to a predetermined time interval 220, or once per a time period.

After normal image 230 is captured, controller 120 transmits the normal image, for example to an example receiver, during transmission time 240. Controller 120 may temporally schedule the capturing and transmission of the normal image to be between capturing of a current probe image (e.g., probe image 210/2) and capturing of a subsequent probe image (e.g., probe image 210/3, which is subsequent to probe image 210/2). Controller 120 may do that according to a 'normal image work cycle', or time period 250 of in-vivo device 100. (Reference numeral 204 denotes a normal image transmission cycle that, as described herein, is variable; that is, its temporal length depends on what probe images 210 captures (images), so normal image transmission cycle 204 may be 'very long' in some instances (when the events of interest are sparse) and 'very short' in others (when the events of interest occur often), and typically between these lengths.)

At time t3 controller 120 operates imager 110 to capture probe image 210/3, and, after comparing it to one or more of past probe images 210/1 and 210/2 (the two probe images previously captured), it determines that in-vivo device 100 is stationary again, or has stopped, and, therefore, controller 120 determines to refrain from operating imager 110 in the superpixel readout mode, so that no normal image is captured, nor does one transmitted, at that time. According to the example timeline shown in FIG. 2B a similar decision is made by controller 120 with respect to time instants t4 through t7, so in-vivo device 100 does not capture (and, therefore, it does not transmit) normal images during the time period t4-t7. This condition changes at time t8.

After controller 120 operates imager 110 at time t8 to capture probe image 210/8 controller 120 may compare probe image 210/8 with any one, or more than one, of probe images 210/1 through 210/7. For example, controller 120 may compare probe image 210/8 only with probe image 210/7, or with probe images 210/7 and 210/6, etc. Assuming that the comparison result indicates to controller 120 that in-vivo device 100 is moving at time t8, or it moved between times t7 and t8, controller 120 operates imager 110 in the single pixel readout mode to capture a normal image 260 before it operates imager 110 again in the superpixel readout mode to capture the next scheduled probe image (probe image 210/9, not shown in the drawing).

After in-vivo device 100 captures normal image 260 controller 120 transmits normal image 260, for example to an example receiver, during transmission time 270. Controller 120 may time the capturing and transmission of the normal image between acquisitions of the currently last probe image (e.g., probe image 210/7) and the currently subsequent, next or scheduled probe image (e.g., probe image 210/9), and do that using the same normal image work cycle 250.

As demonstrated by FIG. 2B, refraining from transmitting normal images whenever in-vivo device 100 is stationary or introduces negligible movement, for example between time instant t3 and t7, saves a considerable amount of battery energy. Battery energy that is saved this way enables in-vivo device 100 to transmit normal images at high rates for longer periods than is the case with conventional in-vivo devices, as exemplified by FIG. 2C, which is described below.

Figure 2C:
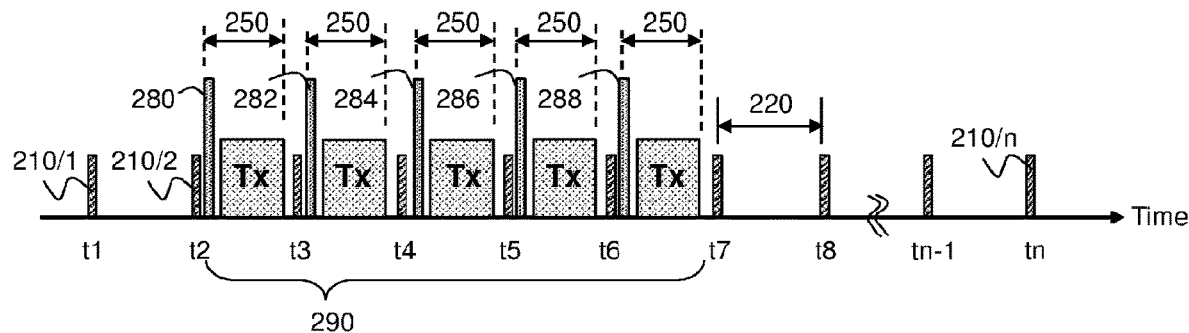
FIG. 2C illustrates the series of probe images of FIG. 2A with normal images interspersed between them according to another example.

FIG. 2C illustrates the series of probe images of FIGS. 2A-2B with normal images interposed between them according to another example. In the example of FIG. 2C controller 120 determined at or for times t2, t3, t4, t5 and t6 that in-vivo device 100 moved after respectively capturing and evaluating probe images 210/2, 210/3, 210/4, 210/5 and 210/6. Accordingly, controller 120 operated imager 110 in the superpixel readout mode to capture and transmit (Tx) a consecutive series 290 of normal images 280, 282, 284, 286 and 288 according to the normal image work cycle 250.

As exemplified in FIGS. 2A-2C, in-vivo device 100 does not operate according to any predetermined image capturing rate or frame transmission rate. Instead, controller 120 captures and transmits normal images ('worthy' images) 'on demand', or whenever circumstances justify capturing and transmitting such images. Controller 120 may decide to capture and transmit normal images on individual bases, regardless of on any predetermined image capturing or image transmitting rate, and thus produce an ad-hoc, instantaneous, image capturing and transmitting rate that can be between zero and a maximum rate that is technically supported by the in-vivo device. The result of such image transmission scheme is that image transmission rate is flexibly and unpredictably variable according to the circumstances. For example, assuming a predetermined probe images time interval 220 is equal to 15.625 milliseconds (msec.), the highest rate, R, at which normal images can be captured and transmitted is sixty four (Rmax=64 FPS) (that is, a normal image may be captured and transmitted every 15.625 msec., that is, one normal image per each probe image), as consecutive series 290 of normal images 280, 282, 284, 286 and 288 (FIG. 2C) demonstrates.

The other extreme in the images capturing and transmission rate, R, is zero (R=0 FPS), as FIG. 2A demonstrates; that is, when no normal images are captured for a relatively long time (e.g., for a few seconds or minutes). FIG. 2B demonstrates an example of 'moderate' (less than the maximum available) capturing and transmission rate, R, where the image capturing and transmission rate R of normal images is between these two extreme rates, in this example it is 12.8 images per second (1/[5×15.625 msec]). Controller 120 may change the normal image capturing (and transmitting) rate R (per, for example, movement of in-vivo device 100) stepwise across multiple rates, where rate R may be calculated using the formula $R=1/(K \times Tp)$, where K is the number of regular probe images that are captured after transmission of a particular normal image and before a subsequent normal image is captured; Tp is the predetermined time interval, shown at 220, from one regular probe image to another). Returning to the example above, for K=1, R=64 FPS (1/15.625 msec.); for K=2, R=32 FPS {1/(2× 15.625 msec.}; for K=3, R=21.3 FPS {1/(3×15.625 msec.}; for K=4, R=16 FPS {1/(4×15.625 msec.}; for K=5 (as in FIG. 2B), R=12.8 FPS {1/(5×15.625 msec.}, and so on.

The capturing and transmission rate of normal images may change between zero and the maximum rate available (64 in the example described above) depending on the determinations of controller 120 regarding movement (for example) of in-vivo device 100, or changes in the scene or scenery imaged by the in-vivo device. As explained herein, controller 120 does not set, use or operate according to any predetermined image transmission rate, as this rate is only a post-factum result of the 'probe image by probe image' determination process, thus it is consequential. If normal images are first stored and accumulated in a memory buffer (e.g., in memory buffer 180), it may occur that multiple images awaiting transmission may be transmitted as one (or in one), long, 'image frame'. The images transmission rate cannot be set in advance because normal images may be accumulated in the memory buffer and transmitted according to changing circumstances (e.g., changing quality of the communication channel, availability of resources inside the in-vivo device, etc.).

Figure 3:
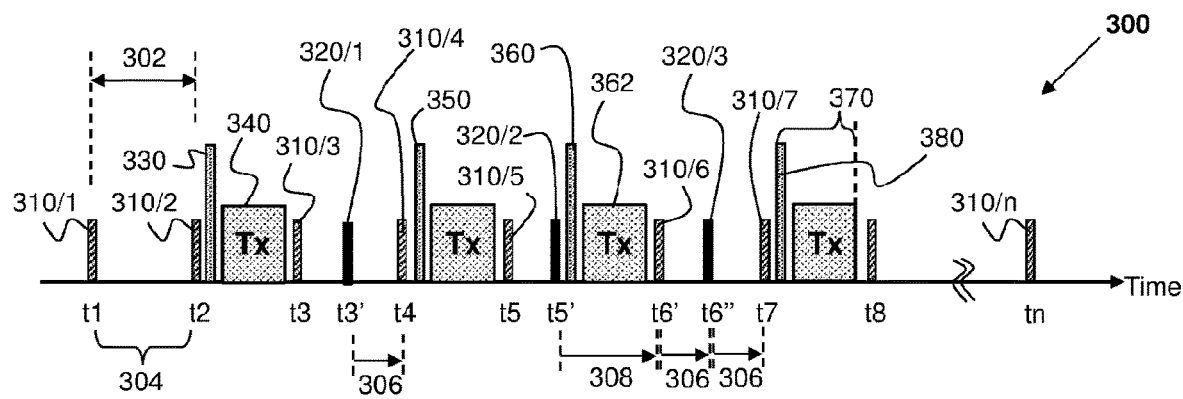
FIG. 3 illustrates a series of probe images that are interposed by intermediate probe images, and normal images that are interspersed between probe images according to another example embodiment.

FIG. 3 illustrates a timeline 300 showing an example series of 'regular' probe images 310/i similar to regular probe image 210/i of FIGS. 2A-2C that are interposed by example conditional probe images (320/i), and example normal images 330, 350, 360 and 380, that are interspersed between probe images according to another example embodiment. (By 'interspersed between probe images' is meant temporally located between two probe images, or between two conditional probe images, or between a probe image and a conditional probe image.) FIG. 3 is described in association with FIG. 1A.

Reference numerals 310/i (i=1, 2, . . . , n) denote a series of probe images that may be similar to, for example, probe images 210/1, 210/2, . . . , 210/n of FIGS. 2A-2C. By way of example, FIG. 3 shows three conditional probe images: reference numeral 320/1 denotes a first conditional probe image that is temporally interposed between probe images 310/3 and 310/4; reference numeral 320/2 denotes a second conditional probe image that is temporally interposed between probe images 310/5 and 310/6, and reference numeral 320/3 denotes a third conditional probe image that is interposed between probe images 310/6 and 310/7.

Controller 120 may initially set imager 110 to capture 'regular' probe images 310/i according to a predetermined time interval 302, as in FIG. 2A. However, per the example of FIG. 3, if controller 120 determines at time t3 that in-vivo device 100 is not moving at time t3, or it has not moved until time t3, controller 120 may use the time period 304 initially allocated for a normal image to capture, at time t3', another probe image (conditional probe image 320/1). That is, controller 120 uses imager 110 to capture an unscheduled probe image between two successive regular probe images 310/i only if there is no justification to capture and transmit a normal image during that time, hence the term 'conditional probe image'. Conditional probe image 320/1 is captured at time t3', which is a middle time between time instant t3 (corresponding to the currently last regular probe image 310/3) and time instant t4 (which corresponds to the next scheduled regular probe image 310/4).

If controller 120 determines that a particular captured conditional probe image does not indicate, in conjunction with another one or more past probe images (conditional or not), that in-vivo device 100 is moving or has moved, controller 120 captures the next regular probe image in a timely manner, according to the initial, predefined, schedule. However, if controller 120 determines that a particular captured conditional probe image indicates that the in-vivo device is moving or has moved, controller 120 executes a normal image work cycle subsequently to the capturing of the last conditional probe image, and delays the capturing of the next regular probe image for a reason that is described below. A conditional probe image may be compared with a past regular probe image and/or with a past conditional probe images and/or with a past normal image.

A fixed time width (T) is allocated to normal image work cycle 370, which is sufficient for both capturing a normal image and transmitting that image. This time width (T) may occupy most of the time period 304 between successive regular probe images; that is, most of the predetermined time interval 302 allocated for regular probe images. As shown in FIG. 3, the time period 370 allocated for a normal image work cycles is greater than the time spacing 306 between each conditional probe image and any adjacent regular probe image. Since controller 120 cannot capture the next regular probe image while it captures and transmits a normal image according to the specified normal image work cycle, controller 120 has to wait a time period 370 before it can do so, and, as describes above, time period 370 is wider than time spacing 306.

At time t5, controller 120 determines that in-vivo device 100 is not moving, or has not moved, and, therefore, controller 120 sets imager 110 to capture conditional probe image 320/2 at time t5', which is a time instant located between the currently last regular probe image 310/5 and the next scheduled regular probe image 310/6. However, at time t5' controller 120 determines, by using conditional probe image 320/2, that in-vivo device 100 is moving, or has moved. Therefore, controller 120 captures normal image 360 and transmits it during transmission period 362. As shown in FIG. 3, capturing normal image 360 and transmitting it during time period 362 enables controller 120 to capture regular probe image 310/6 only after an extended time period 308 (that is, at time t6'). Time period 308 is extended relative to (it is longer than) the initially scheduled time period 306, which is shorter. (Time instant t6' is delayed with respect to time t6 in FIGS. 2A-2C.) At time t6', controller 120 determines to refrain from capturing and transmitting a normal image and, therefore, controller 120 may reuse the predetermined interval time allocated for regular probe images as a basis for continuing capturing probe images, for example for capturing conditional probe image 320/3 and subsequent regular probe image 310/7. If another conditional probe image indicates to controller 120 that in-vivo device 100 is moving, or has moved, controller 120 captures and transmits another normal image (using the same predefined work cycle 370) and, again, delays the capturing of the next regular probe image until after the transmission of the normal image ends.

Figure 4:
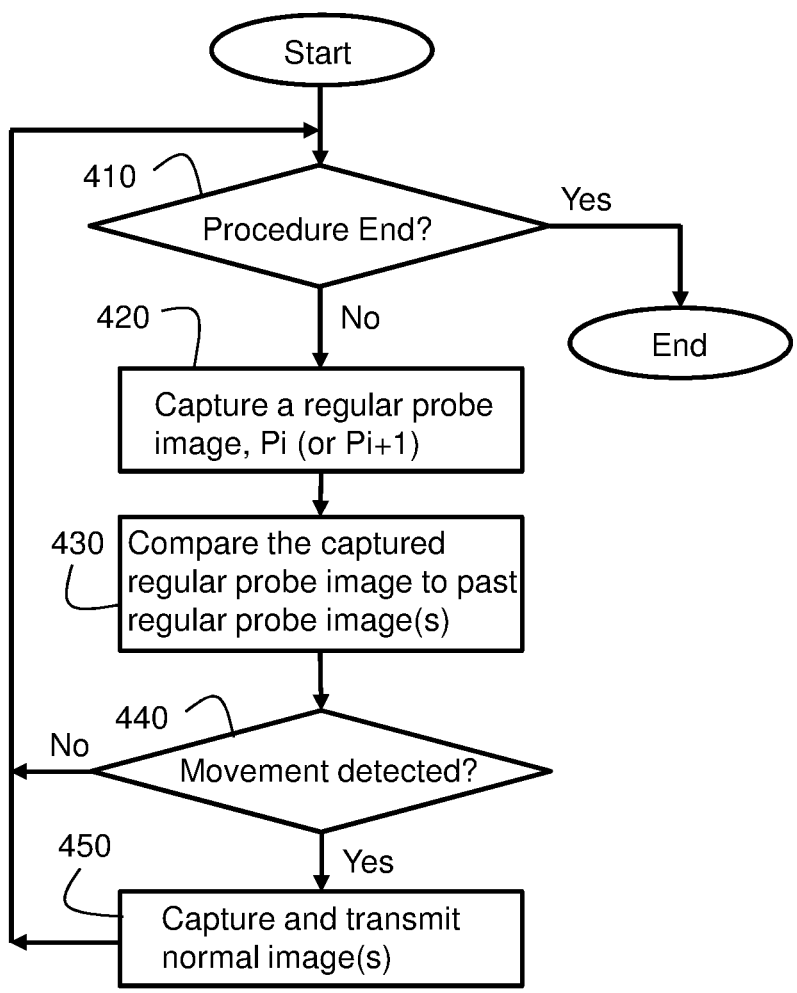
FIG. 4 shows a method for transmitting normal images by an in-vivo device according to an example embodiment.

FIG. 4 shows a method for transmitting normal images by an in-vivo device according to an example embodiment. (FIG. 4 is described in association with FIG. 1A.) At step 410, controller 120 may check whether an imaging procedure is to be, or has been, terminated. If it is not to be terminated, or has not been terminated (this condition is shown as "No" at step 410), controller 120 may, at step 420, operate pixel array 130 in the superpixel readout mode and, using this pixel readout mode, controller 120 may capture a regular probe image, Pi. At step 430, controller 120 compares the regular probe image with past regular probe image(s), that is, if there is at least one previously captured regular probe image to compare it to. At step 440, controller 120 checks whether the comparison result indicates that in-vivo device 100 is moving or has moved. If controller 120 determines that the comparison result indicates that in-vivo device 100 is moving or has moved (this condition is shown as "Yes" at step 440), controller 120 operates pixel array 130 in the single pixel readout mode and, using this pixel readout mode, controller 120 may capture and transmit (e.g., to an external receiver), at step 450, a normal image or a series (burst) of normal images. (A burst of normal images ('image burst' for short) may include one normal image or more than one normal image; e.g., three normal images, five normal images, etc.) However, if controller 120 determines that the comparison result does not indicate that in-vivo device 100 is moving or that in-vivo device 100 has not moved (this condition is shown as "No" at step 440), controller 120 may continue to operate pixel array 130 in the superpixel readout mode and capture, at step 420, another (a subsequent) regular probe image, Pi+1. The highest FPS rate may occur when each regular probe image results in the transmission of a normal image. The FPS capturing and transmission rate may be zero when none of the regular probe images results in the transmission of a normal image.

Figure 5:
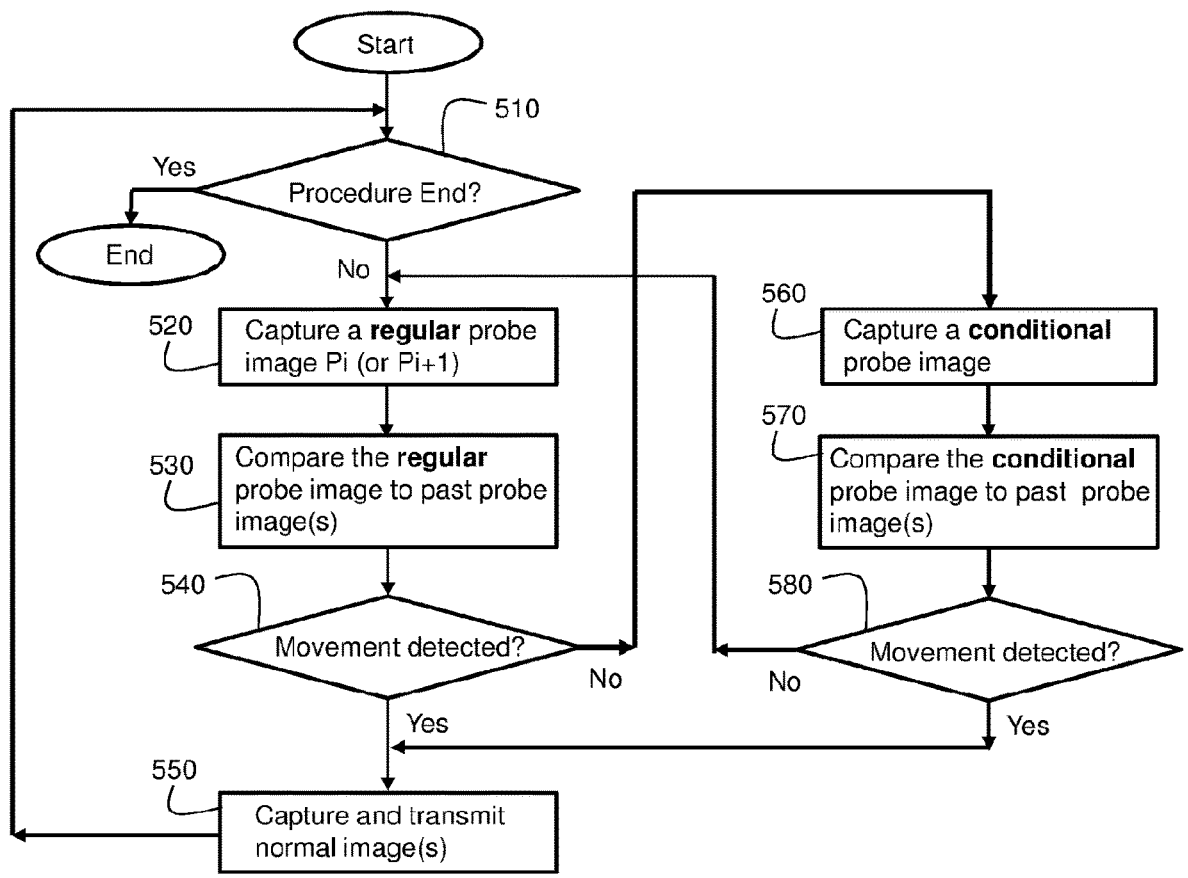
FIG. 5 shows a method for transmitting normal images by an in-vivo device according to another example embodiment.

FIG. 5 shows a method for transmitting normal images by an in-vivo device according to another example embodiment. (FIG. 5 is described in association with FIG. 1A.) At step 510, controller 120 may check whether an imaging procedure is to be, or has been, terminated. If it is not to be terminated, or has not been terminated (this condition is shown as "No" at step 510), controller 120 may, at step 520, operate pixel array 130 in the superpixel readout mode and, using this pixel readout mode, controller 120 may capture a regular probe image, Pi. At step 530, controller 120 compares the regular probe image with past regular probe image(s) and/or with past conditional probe image(s), that is, if there is at least one previously captured regular probe image and/or conditional probe image(s) to compare it to. At step 540, controller 120 checks whether the comparison result indicates that in-vivo device 100 is moving or has moved. If controller 120 determines that the comparison result indicates that in-vivo device 100 is moving or has moved (this condition is shown as "Yes" at step 540), controller 120 may operate pixel array 130 in the single pixel readout mode and, using this pixel readout mode, controller 120 may capture and transmit (e.g., to an external receiver), at step 550, a normal image or a series (burst) of normal images. (An image burst may include one normal image or more than one normal image; e.g., three normal images, five normal images, etc.). However, if controller 120 determines that the comparison result does not indicate that in-vivo device 100 is moving or has not moved (this condition is shown as "No" at step 540), controller 120 may continue to operate pixel array 130 in the superpixel readout mode in order to capture, at step 560, a conditional probe image.

At step 570, controller 120 compares the conditional probe image with past regular probe image(s) and/or with past conditional probe image(s), that is, if there is at least one previously captured regular probe image and/or conditional probe image(s) to compare it to. At step 580, controller 120 checks whether the comparison result indicates that in-vivo device 100 is moving or has moved. If controller 120 determines that the comparison result indicates that in-vivo device 100 is moving or has moved (this condition is shown as "Yes" at step 580), controller 120 may operate pixel array 130 in the single pixel readout mode and, using this pixel readout mode, controller 120 may capture and transmit (e.g., to an external receiver), at step 550, a normal image or a series (burst) of normal images. However, if controller 120 determines that the comparison result does not indicate that in-vivo device 100 is moving or has not moved (this condition is shown as "No" at step 580), controller 120, by returning to step 520, may reuse the superpixel readout mode of pixel array 130 in order to capture a new (e.g., subsequent) regular probe image.

A difference between the methods shown in FIG. 4 and FIG. 5 is that the time spacing (time window) between the capturing time of a conditional probe image and the capturing time of a regular probe image is less, or shorter, than the predetermined time interval of the regular probe images. Another difference is that while regular probe images are always captured (according to a predetermined time interval), hence the term 'regular probe images', conditional probe images are captured only if a regular probe image does not result in a capturing and transmission of a normal image, hence the term 'conditional probe image, in which case controller 120 may utilize the time slot between adjacent regular probe images to capture an 'earlier' probe image (instead of capturing a normal image). (A conditional probe image may be thought of as an earlier probe image, or an un-prescheduled probe image.) A conditional probe image may be thought of as a regular probe image that is captured (and used) earlier than originally scheduled by the predetermined time interval governing capturing of the regular images.

Referring to FIG. 4 and FIG. 5, it may occur that the result of comparing between any two particular regular probe images, or between any regular probe image and conditional probe image, or between any two conditional probe images would result in an image burst that includes one or more normal images. The number of normal images that are to be captured and transmitted in an image burst may be predetermined and depend on the event indicated, or detected, by the comparison result. For example, if two or more regular probe images are compared and the comparison result(s) indicates, with relatively high probability (e.g., higher than 70%), detection of, for example, a polyp, then it may be predetermined to capture and transmit an image burst that includes, for example, six normal images in order to ensure that the GI 'site' suspected to be a polyp and its 'close' environment are imaged, rather being missed by the in-vivo device. In another example, if a regular probe image is compared to another regular probe image and the comparison result suggests the detection of, for example, disseminated disease (e.g., Crohn's disease, bleeding, etc.), then it may be predetermined to capture and transmit an image burst that includes, for example, twenty five normal images in order to enable evaluation of the severity of the disease.

FIGS. 4 and 5, by way of example, show that regular probe images and conditional probe images can be compared in order to detect movement of an in-vivo device, and that movement of the in-vivo device can be used to trigger capturing and transmission of normal images. In a more general case, the trigger to the capturing and transmission of normal images may be any predetermined event, and the event that triggers a capturing and transmission of one or more (e.g., burst) normal images may be detected by using one or more probe images, and, optionally, also normal images.

Figure 6:
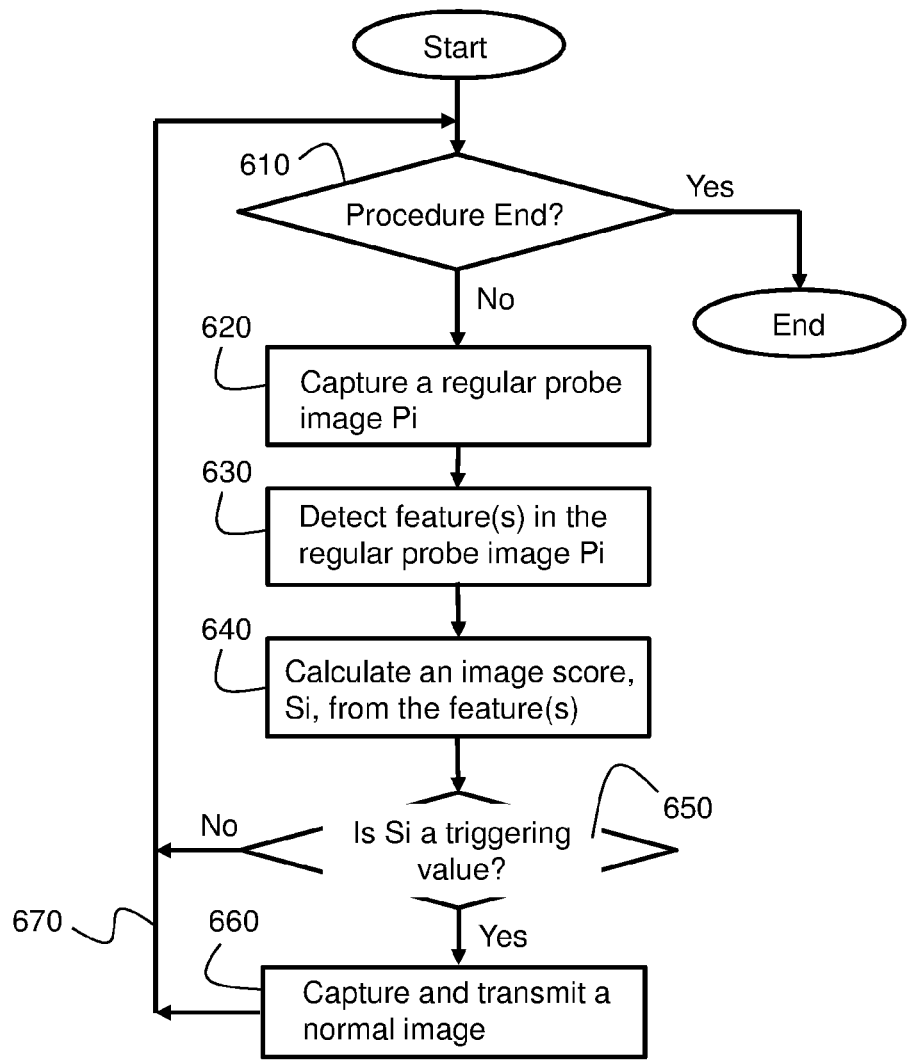
FIG. 6 shows a method for capturing and transmitting normal images by an in-vivo device during an imaging procedure according to another example embodiment.

FIG. 6 shows a method for capturing and transmitting normal images by an in-vivo device during an imaging procedure according to another example embodiment. (FIG. 6 is described in association with FIG. 1A.) The method shown in FIG. 6 includes triggering the capturing and transmission of normal images based on one regular probe image at a time; that is, based on individual regular probe images.

Controller 120 may use pixels readout circuit 140 to operate imager 110 in the superpixel readout mode according to a time interval in order to capture a series of regular probe images designated as P1, P2, P3, . . . , Pn. (Operating imager 110 in a particular pixel readout mode and operating pixel array 130 in that particular pixel readout mode are analogous in that both instances may have the same result, which is capturing a regular probe image whenever the superpixel readout mode is used, and capturing (and transmitting) a normal image, or a series of normal images, whenever the single pixel readout mode is used.)

At step 610, controller 120 checks whether the imaging procedure is still on. If the imaging procedure is still on (this condition is shown as "No" at step 610), controller 120 may, at step 620, operate pixel array 130 in the superpixel readout mode and, using this pixel readout mode, controller 120 may capture a regular probe image, Pi, which, as described herein, is frugal in terms of resources and battery power use. At step 630, controller 120 may detect a feature, or features, in the captured regular probe image (Pi) and, at step 640, controller 120 may calculate an image score, Si, for that regular probe image based on, or using, the detected feature(s). A 'feature', or a 'parameter', in an image may be anything in the image (e.g., a particular color or color combination, discernible boundary or boundaries that define an image shape, an organ or lines, a particular image property or parameter; e.g., pixel values, imager parameter; e.g., gain, light exposure time, etc.) that may be or represent anything of clinical or pathological importance, for example polyps, ulcers, etc., or an organ of the GI tract, or a landmark or location in the GI tract, etc. Typically, a combination or set of features may be required in order to detect something of clinical or pathological importance, or to detect a usable landmark.

The feature, or features, which controller 120 may be configured or trained to detect at step 630, may be indicative of, related to or represent a 'triggering event', or an event of interest, that may be selected from the group consisting of, for example: movement of the in-vivo device, a particular GI segment or location in the GI tract the in-vivo device is at, a particular landmark in the GI tract, a pathology (e.g., polyp, ulcer, etc.), a changed scene (or scenery), etc. (A 'triggering event' means herein an event of interest that a probe image or a group of successive probe images captures, which result in capturing and transmission of one normal image or of a series ('burst') of normal images.)

Controller 120 may calculate image score Si, at step 640, by applying, for example, a rule-based system, or one or more classification methods (e.g., support vector machines ("SVM"), decision trees, etc.), or any combination thereof, to the detected features. The value of image score Si may be, or represent, a probability that the probe image has captured a triggering event. A 'triggering score' is a score value that is equal to or greater than a predetermined threshold value above which it is determined or concluded that the probe image has captured a triggering event (e.g., an event of interest).

At step 650, controller 120 checks whether score Si is a triggering score. If controller 120 determines that the score is a triggering score (this condition is shown as "Yes" at step 650), controller 120 operates pixel array 130 in the single pixel readout mode and, using this pixel readout mode, controller 120 captures and transmits (e.g., to an external receiver), at step 660, a normal image, or a series of normal images. Then, if the imaging procedure has not yet terminated (per step 610), controller 120 may repeat (670) steps 620, 630, that is, it may operate pixel array 130 in the superpixel readout mode and capture a subsequent regular probe image, Pi+1, then it may detect feature(s) in regular probe image Pi+1, calculate a score for regular probe image, Pi+1, and so on.

However, if controller 120 determines that the score is not a triggering score (this condition is shown as "No" at step 650), which means that no normal image is to be captured, controller 120 continues to operate pixel array 130 in the superpixel readout mode in order to capture a next regular probe image, Pi+1. Controller 120 may repeat steps 620 through 660 until the imaging procedure is terminated at step 610. As exemplified by FIG. 6, capturing and transmission of a normal image (or of a series of normal images) is conditional because these operations may take place only when this is justified clinically, per the latest captured regular probe image or normal image, and/or per one or more regular probe images that were captured already and/or per one or more normal images that were already captured.

In some embodiments, after a particular score is determined to be a triggering score, controller 120 may capture and transmit a normal image, or a series (a burst) of predetermined number of normal images, with the number of normal images being fixed or dependent on one or more factors. For example, the number of normal images in an image burst may depend on the location of the in-vivo device in the GI tract, or on the type of pathology in the probe image, or on a landmark detected by using the probe image (or by using a normal image), etc. (An image burst may include any number of normal images, including one normal image.)

Figure 7:
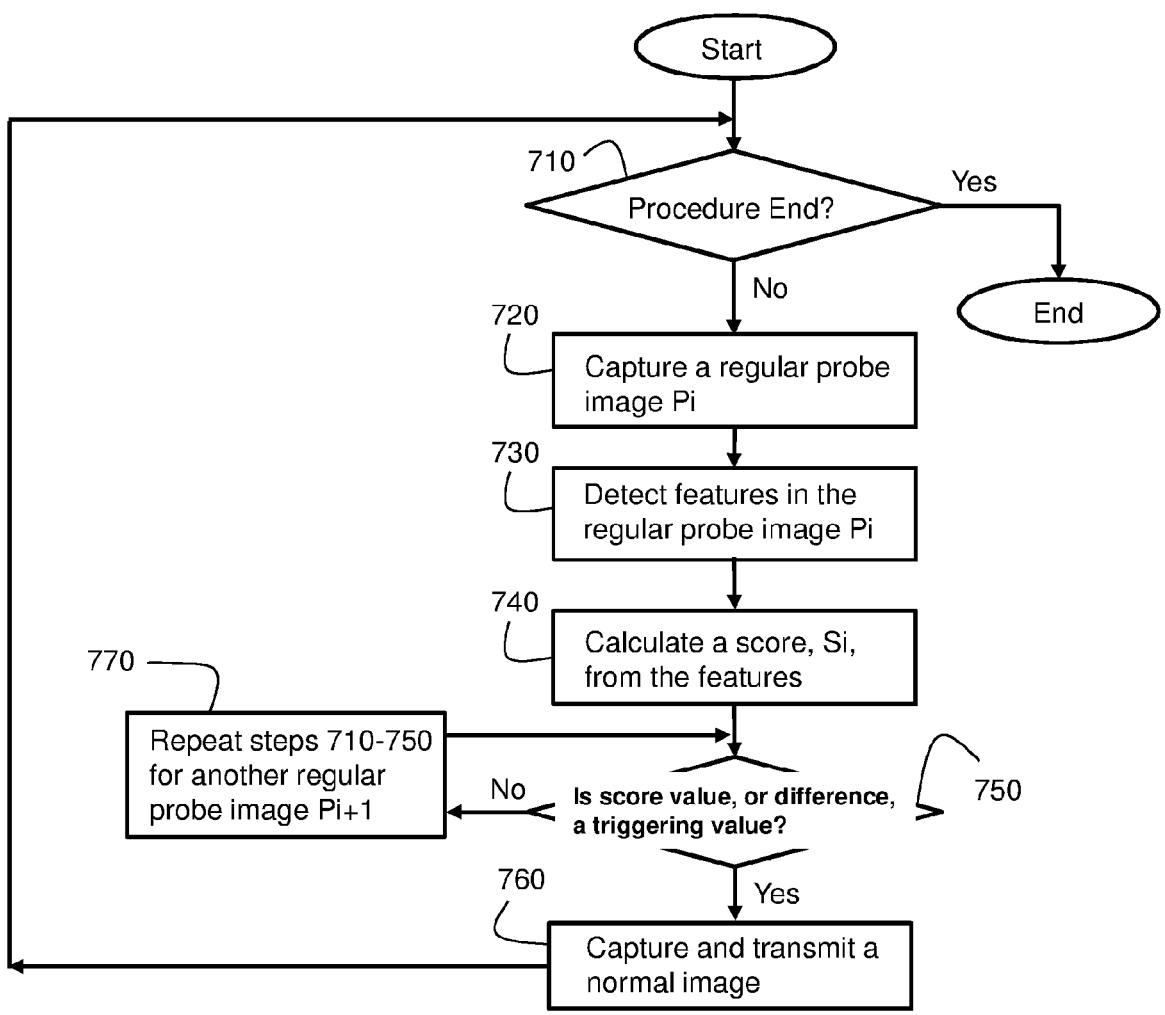
FIG. 7 shows a method for triggering the capturing and transmission of normal images based on one or more probe images.

While FIG. 4 shows a method for triggering capturing and transmission of normal images based on comparison between probe images, and FIG. 6 shows a method for triggering capturing and transmission of normal images basically based on one regular probe image at a time, FIG. 7 shows a method for triggering the capturing and transmission of normal images based on one or more probe images. That is, a decision to capture and transmit a normal image (or a normal image burst) may be made (e.g., by controller 120) either by using one regular probe image, or by two or more regular probe images.

Referring to FIG. 7 (which is described below in association with FIG. 1A), at step 710, controller 120 may check whether the imaging procedure is still on. If the imaging procedure is still on (this condition is shown as "No" at step 710), controller 120 may perform, or execute, steps 720, 730 and 740, which may be respectively identical or similar to steps 620, 630 and 640 of FIG. 6. At step 720, controller 120 operates pixel array 130 in the superpixel readout mode in order to capture a regular probe image.

At step 750, controller 120 checks whether the score that it calculated for the probe image is a triggering score (that is, if the image involved indicates an event of interest). If controller 120 determines that the score is a triggering score (this condition is shown as "Yes" at step 750), controller 120 operates pixel array 130 in the single pixel readout mode in order to capture and transmit (e.g., to an external receiver), at step 760, a normal image, or a series of normal images. In some embodiments, controller 120 may capture and transmit a series (a burst) of normal images, where the number of normal images in the series of images may be fixed or context-dependent; e.g., the number of images in an image burst may depend on one or more factors, for example on the location of the in-vivo device in the GI tract, the type of pathology in the probe image, a landmark detected by the probe image, etc. (An image burst may include one normal image or more than one normal image.) However, if controller 120 determines that the score is not a triggering score (this condition is shown as "No" at step 750); that is, if the image involved does not indicate an event of interest), controller 120 may reuse pixel array 130 in the superpixel readout mode and repeat steps 720 through 750 (unless the imaging procedure has terminated, per step 710), at step 770, in order to capture a second (another, or subsequent) probe image and calculate a score value for the second probe image. At step 750, controller 120 may check the score value of the second probe image in order to determine whether the score of the second probe image is a triggering score (that is, if the image involved indicates an event of interest). If controller 120 determines that the score of the second probe image is a triggering score (this condition is shown as "Yes" at step 750); that is, if the image involved indicates an event of interest, controller 120 may transition pixel array 130 from the superpixel readout mode to the single pixel readout mode in order to capture and transmit, at step 760, a normal image or a series (a burst) of (e.g., predetermined, or conditional) number of normal images. Transitioning a pixel array from the superpixel readout mode to the single pixel readout mode, and vice versa, may mean controlling, by a controller (e.g., controller 120), a pixel readout circuit (e.g., pixels readout circuit 140) such as to select a pixel readout circuit corresponding to a wanted mode, for example using pixel readout circuit 142 to read superpixels, and pixel readout circuit 144 to read pixels individually. Different algorithms may also be involved in using the two pixel readout circuits (142, 144).

However, if controller 120 determines that the score of the second regular probe image is also not a triggering score (that is, if the images involved do not indicate an event of interest), controller 120 may further check whether a difference score is a 'triggering difference score'. A difference score is a difference between a particular score value calculated for a regular probe image Pi and a score value calculated for a subsequent regular probe image Pi+1. A difference score is a 'triggering difference score' (or a triggering score) if its value is equal to or greater than a threshold value above which it is determined or concluded that two regular probe images jointly (a difference between the two images) indicate a triggering event (an event of interest). That is, it may occur that neither a particular regular probe image nor a subsequent regular probe image indicate any event of interest, but differences between these two regular probe images, or differences between one or more regular probe images and one or more normal images, may indicate an event of interest. A difference between regular probe images may be derived or calculated from, or using, the respective scores. Alternatively, a difference score between regular probe images may be calculated based on feature(s) in the regular probe images that are compared. If controller 120 determines that the difference score is not a triggering score either (this condition is shown as "No" at step 750); that is, the involved images do no indicate an event of interest, controller 120 may operate (e.g., reuse) pixel array 130 in the superpixel readout mode and repeat steps 720 through 750 in order to capture and process another (e.g., subsequent) probe image, and so on, until the imaging procedure is terminated, per step 710.

Figure 8:
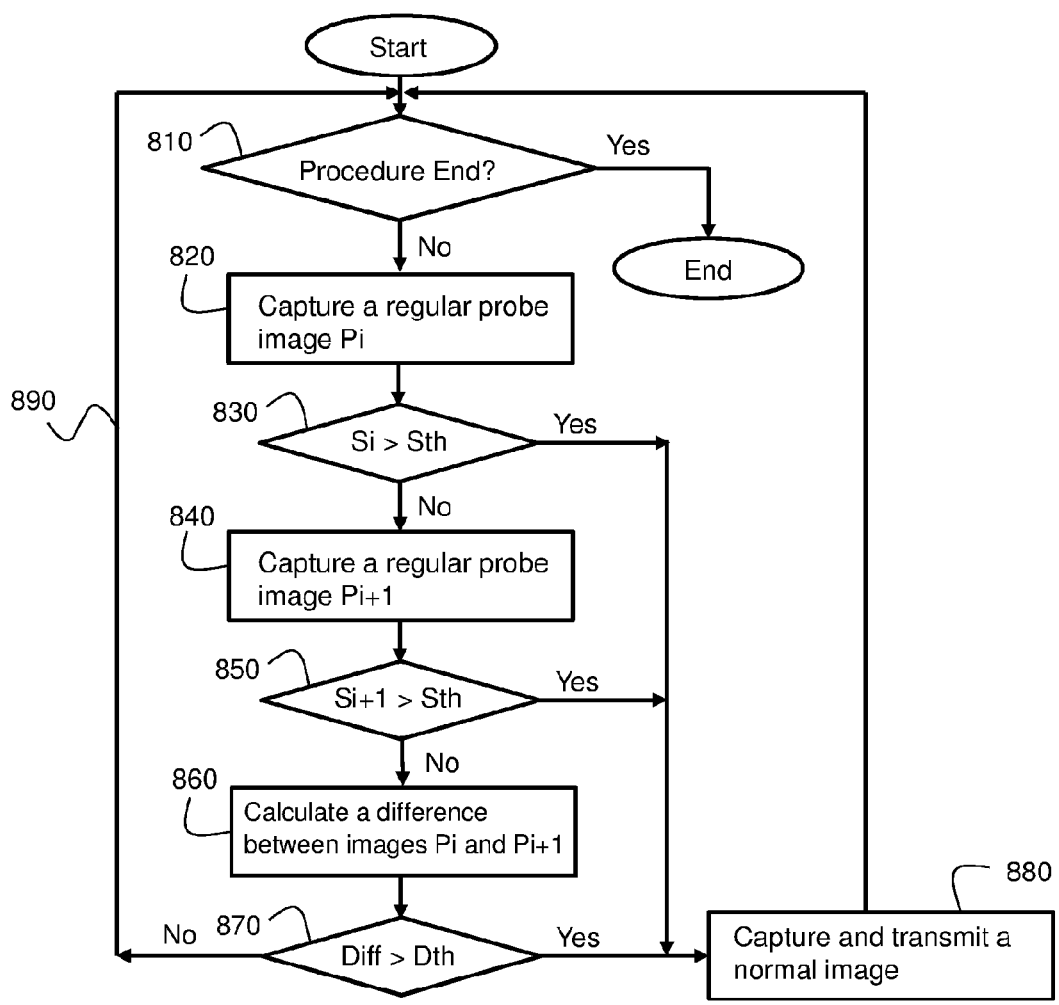
FIG. 8 shows a method for capturing and transmitting normal images according to another example embodiment.

FIG. 8 shows a method for capturing and transmitting normal images according to another example embodiment. The method described in connection with FIG. 8 (and also with the other drawings) is performed by an in-vivo device (e.g., in-vivo device 100) moving in the gastrointestinal tract, and the in-vivo device may include, among other things, a pixel array (pixel array 130), where the pixel array is operable in a superpixel readout mode of operation in which the pixel array captures regular probe images by reading clusters of pixels, and in a single pixel readout mode of operation in which the pixel array captures normal images by reading pixels individually. (The method shown in FIG. 8 is described in association with FIG. 1A.)

At step 810, controller 120 may check whether the imaging procedure is still on. If the imaging procedure is still on (this condition is shown as "No" at step 810), controller 120 may, at step 820, operate pixel array 130 in the superpixel readout mode in order to capture a regular probe image Pi, and, in addition, calculate a score, Si, from (based on) feature(s) in the regular probe image Pi.

At step 830, controller 120 may determine whether the score Si is a triggering score. If controller 120 determines that the score Si is not a triggering score (this condition is shown as "No" at step 830), controller 120 may, at step 840, continue to operate the pixel array in the superpixel readout mode to capture a subsequent regular probe image Pi+1, and, in addition, calculate a score, Si+1, from (based on) feature(s) in the subsequent regular probe image Pi+1. If controller 120 determines that the score Si+1 is also not a triggering score (this condition is shown as "No" at step 850), controller 120 may, at step 860, calculate a difference score representative of a difference between the regular probe images.

Controller 120 may calculate a difference score based on, for example, features in the regular probe image Pi and features in the regular probe image Pi+1, or based on the scores Si and Si+1, etc. Controller 120 may, at step 860, compare between any probe image (regular probe image or conditional probe image) that controller 120 currently captures to any one or more probe images (regular probe image(s) or conditional probe image(s)) that controller 120 previously captured in order to detect an event of interest. Controller 120 may compare between any two images by, for example, detecting features in the compared images and calculating differences between detected features. Controller 120 may alternatively or additionally compare between any two images by comparing an image parameter or image parameters that are related to the compared images. (An image parameter may be, for example, an image color or image colors, an amplifier gain that is used to amplify a pixel output signal or a superpixel output signal, or an imaging exposure time, etc.) Controller 120 may calculate a difference score that reflects a difference or differences between two images or between more than two images (e.g., a series of images), and one of the compared images may be the currently captured probe image (e.g., the last probe image that is captured by the time that a difference score is calculated).

If controller 120 determines that the difference score is also not a triggering difference score (this condition is shown as "No" at step 870), controller 120 may repeat loop 890 (steps 810-870). (If controller 120 determines that none of the scores (or features) calculated for (or detected in, or derived from) the regular probe images already captured indicates or suggests an event of interest (e.g., an event justifying transmission of a normal image, or an image burst), controller 120 may repeat loop 890 until one or more regular probe images collectively indicate or suggest that they captured an event of interest.) However, if the score Si is a triggering score (this condition is shown as "Yes" at step 830), or if the score Si+1 is a triggering score (this condition is shown as "Yes" at step 850), or if the difference score Si is a triggering difference score (this condition is shown as "Yes" at step 870), then controller 120 may, at step 880, operate the pixel array in the single pixel readout mode and capture and transmit a normal image, or a series (burst) of normal images, before controller 120 transitions the pixel array back to the superpixel readout mode and captures a subsequent regular probe image.

A score Si is regarded as a triggering score if its value is equal to or greater than a threshold value, Sth, and a difference score is regarded as a triggering difference score if its value is equal to or greater than a threshold value, Dth. A controller (e.g., controller 120) may use a feature, or a set of features, that it identifies in an image, or that it calculates from or based on an image, per se, that is, a score need not be calculated from them, or the controller may use a feature, or features, to calculate, therefor, a score that may represent the image. A threshold value may be fixed for all captured images. Alternatively, a threshold value, which the controller may apply to a subsequent probe image, may depend on information that the controller obtains from already captured images. A threshold value may be determined for a subsequent probe image based on an event of interest that is identified or detected in past probe image or past probe images. (In one example, the lower a threshold value, the higher the probability that the controller will capture and transmit a normal image, or an image burst.)

In some embodiments, the configuration of superpixels used to capture probe images may be selected based on the type of event of interest (for example depending on which type of event of interest is searched for). For example, some superpixel configurations may be (more) sensitive to movement of the in-vivo device; other superpixel configurations may be (more) sensitive to a particular pathology (e.g., polyps); other superpixel configurations may be (more) sensitive to a particular landmark or segment of the in-vivo device in the GI tract (e.g., entrance to the colon).

Figure 9:
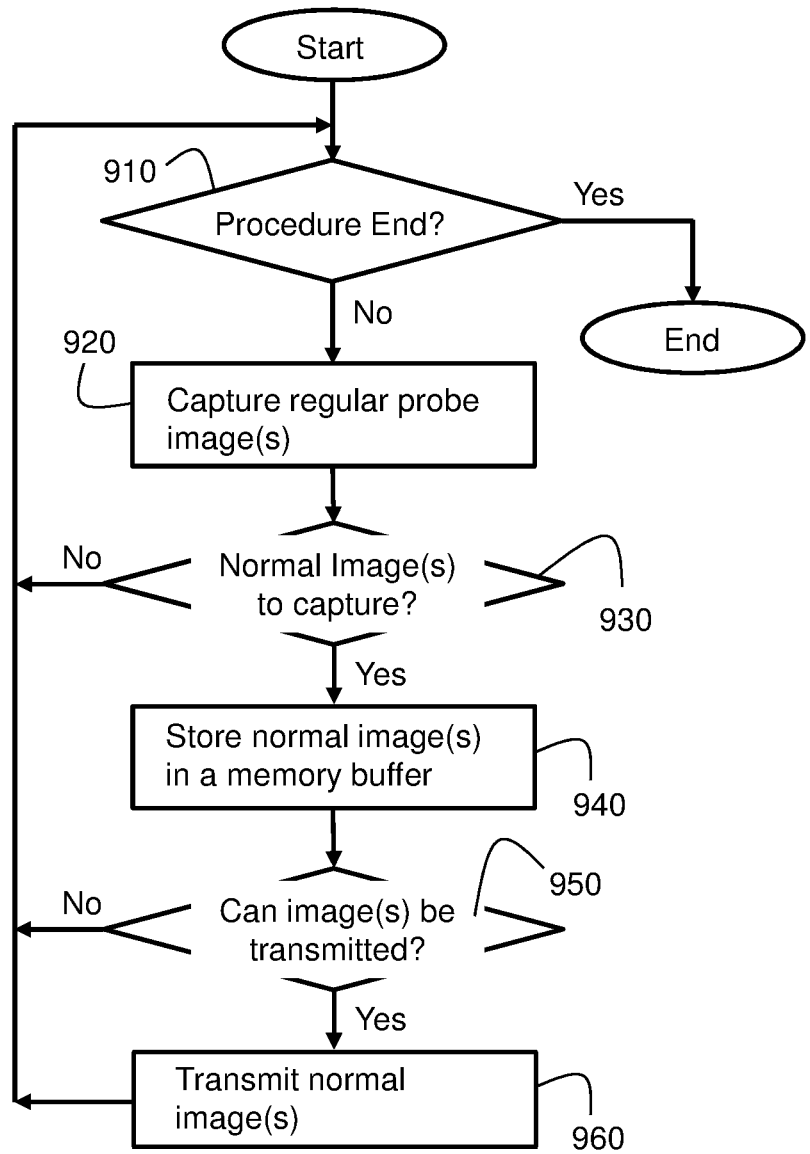
FIG. 9 shows a method of transmitting normal images according to yet another example embodiment.

FIG. 9 shows a method of transmitting normal images according to another example embodiment. (FIG. 9 is described in association with FIG. 1A.) At step 910, controller 120 may check whether the imaging procedure is still on. If the imaging procedure is still on (this condition is shown as "No" at step 910), controller 120 may, at step 920, operate pixel array 130 in the superpixel readout mode in order to capture a regular probe image.

At step 930, controller 120 may evaluate the probe image, or probe images, for example by using or comparing image features or image parameters, or a score value of one or more probe images, and, based on comparison process, controller 120 may determine whether a normal image (or an image burst) should be transmitted. If controller 120 determines, at step 930, that a normal image (or a series of images) is to be captured and transmitted (this condition is shown as "Yes" at step 930), controller 120 may, at step 930, capture a normal image, or a series of normal images, and, at step 940, it may temporarily store the normal image (or the series of normal images) in memory buffer 180, for example until controller 120 can transmit them, given resources and timing constraints which in-vivo device 100 is subjected to.

At step 950, controller 120 checks whether a current operational state or condition of the in-vivo device permits the transmission of one or more of the normal images that are stored in memory buffer 180. If controller 120 determines that one or more of the stored normal images can be transmitted (this condition is shown as "Yes" at step 950), controller 120 transmits, at step 960, as many stored normal images as possible, with the number of temporarily stored normal images that can be transmitted at each transmission period being subjected to the resources and timing constraints under which in-vivo device 100 operates.

If controller 120 determines, at step 930, that no normal image should be captured (this condition is shown as "No" at step 930), controller 120 may repeat step 920 in order to capture another probe image(s) for evaluation, and so on. If controller 120 determines, at step 950, that none of the stored normal images can be transmitted at this stage (this condition is shown as "No" at step 950), for example because controller 120 is busy in other tasks, or a new probe image is being capture, controller 120 refrains from transmitting any normal image and, instead, controller 120 may repeat step 920 in order to capture (and temporarily store in memory buffer 180) another probe image for evaluation, and so on.

In some embodiments, steps 920 and 960 may not be allowed to be performed at the same time because of, for example, battery power considerations (e.g., high current peak, etc.). However, in other embodiments, by properly designing the power source that powers in-vivo device 100 (e.g., using a separate battery for each function) and the way data is stored in and read from memory buffer 180, steps 920 and 960 may be performed substantially at the same time. That is, using meticulous design, normal images may be transmitted, at step 960, at substantially the same time when a probe image is captured, at step 920.

Similarly, in some embodiments steps 930 (capturing a normal image) and 960 (transmitting one or more stored normal images) may not be allowed to be performed at the same time because of, for example, battery power considerations (e.g., high current peak, etc.). However, in other embodiments, by properly designing the power source that powers in-vivo device 100 (e.g., using a separate battery for each function) and the way data is stored in and read from memory buffer 180, steps 930 and 960 may be performed substantially at the same time. That is, using meticulous design, normal images may be transmitted, at step 960, at substantially the same time when another normal image is captured, at step 930.

Figure 10:
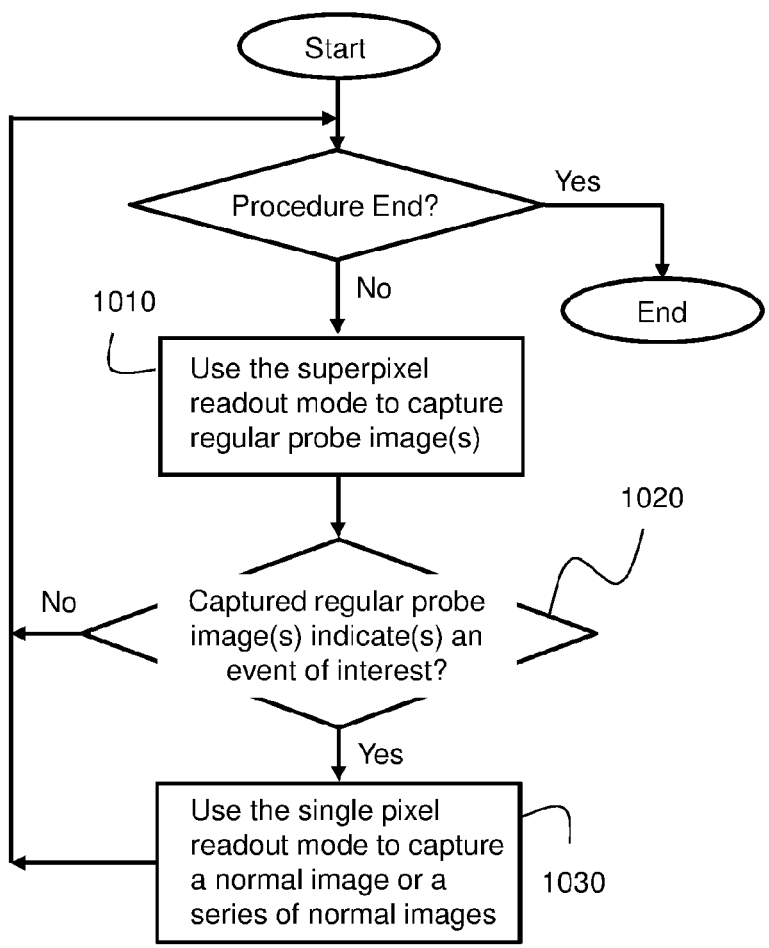
FIG. 10 shows a method of transmitting normal images according to yet another example embodiment.

FIG. 10 shows a method for transmitting images by an in-vivo device swallowed by a subject according to another example embodiment. (FIG. 10 is described in association with FIG. 1A.) The embodiment may be implemented by controller 120, and in-vivo device 100 includes a pixel array 130 operable in a superpixel readout mode of operation in which pixel array 130 captures regular probe images by reading clusters of pixels, and in a single pixel readout mode of operation in which pixel array 130 captures normal images by reading the pixels individually.

Referring to FIG. 10, while the imaging procedure is on the following operations are performed. At step 1010, controller 120 uses the superpixel readout mode to capture a current regular probe image. At step 1020, controller 120 determines whether the currently captured regular probe image (either individually or in comparison to past captured regular probe(s)) indicates an event of interest. If controller 120 determines that the currently captured regular probe image (individually or in comparison to past captured regular probe(s)) does not indicate an event of interest (this condition is shown as "No" at step 1020), controller 120 repeats steps 1010 and 1020, taking into account a subsequently captured regular probe image. However, if at step 1020 controller 120 determines that the currently captured regular probe image (individually or in comparison to past captured regular probe(s)) indicates an event of interest (this condition is shown as "Yes" at step 1020), controller 120 uses, at step 1030, the single pixel readout mode to capture a normal image or a series (burst) of normal images, and repeats steps 1010 through 1030. Controller 120 may operate pixel array 130 in the superpixel readout mode according to a predetermined time interval.

Controller 120 may, at step 1010, calculate a score for each currently captured regular probe image, and (i) if, per step 1020, controller 120 determines that a score of a currently captured regular probe image, either individually or in comparison to (in conjunction with, or based also on) scores of previously captured regular probe image, does not indicate an event of interest, controller 120 may capture a subsequent regular probe image, at step 1010, by operating pixel array 130 in the superpixel readout mode, and calculate a score for the subsequent regular probe image, and (ii) if, per step 1020, controller 120 determines that the score of the currently captured regular probe image, individually or in comparison to scores of previously captured regular probe image, indicates an event of interest, controller 120 may capture, for transmission, at step 1030, a normal image or a series of normal images by operating pixel array 130 in the single pixel readout mode, and, then, capture, at step 1010, a subsequent regular probe image and repeat steps (i)-(ii).

Controller 120 may calculate a difference score between a score of a currently captured regular probe image, wherein a score of each regular probe image equal to or greater than a first threshold and a difference score equal to or greater than a second threshold indicate an event of interest. Controller 120 may set the number of normal images in the series of normal images to a number dependent on the indicated event of interest. Controller 120 may select a superpixel configuration for the superpixel readout mode according to the indicated event of interest or according to an anticipated event of interest. An event of interest may be anticipated from, or based on, information (e.g., scores, image features, sensory information, etc.) that the in-vivo device may collect by using its sensors, and a superpixel configuration which is more suitable for the anticipated event may be selected.

Controller 120 may select or determine a threshold value for a score of a regular probe image based on an event of interest that is detected by using already captured regular probe image(s). Controller 120 may use a sensor in the in-vivo device to sense a non-image parameter of the GI tract and/or of in-vivo device 100 to corroborate an (initially) indicated event of interest. The non-image parameter may be selected from the group consisting of: movement, acceleration, acidity (pH), pressure and temperature. (Other or additional non-image parameter may be selected.) The event of interest may be selected from for example movement of the in-vivo device relative to a scene imaged by the in-vivo device or relative to a change in the scene or relative to a landmark in the GI tract, a landmark in the GI tract, a particular location or segment in the GI tract, an organ of the GI tract, and a pathology. (Other or additional events of interest may be used.) The pathology may be selected from the group consisting of polyp, ulcer, diverticulum, bleeding and Crohn's disease. (Other or additional pathologies may be used.)

Controller 120 may calculate a score for a particular regular probe image based on an image parameter or an image feature that may be detected in, or which is related to or derived from the particular regular probe image. Controller 120 may alternatively or additionally calculate a score for a particular regular probe image based on an imaging amplifier gain and an imaging light exposure time involved in capturing a regular probe image, a conditional probe image or a normal image. Controller 120 may operate illumination source 112 in a first illumination mode when pixel array 130 is operated in the superpixel readout mode, and in a second illumination mode different than the first mode when pixel array 130 is operated in the single pixel readout mode. The first illumination mode may involve using the illumination source in less than an optimal illumination level (e.g., in a power saving mode), and the second illumination mode may involve using the illumination source in an optimal illumination level.

Controller 120 may capture, by using the superpixel readout mode, a conditional probe image between two successive regular probe images if no normal image is to be captured between the two successive regular probe images. Controller 120 may compare the conditional probe image with a past regular probe image(s) and/or with a past conditional probe image(s) and/or with a past normal image(s) and, based on the comparison results, determine whether an event of interest is indicated. Controller 120 may store each captured normal image in memory buffer 180, and use transceiver 114 to orderly transmit the stored normal images to an external receiver according to a transmission queue.

Also provided is a swallowable in-vivo device, wherein the in-vivo device includes a pixel array (e.g., pixel array 130) comprising image pixels, and a controller (for example controller 120). The controller may be configured to operate the pixel array (e.g., according to a time interval; e.g., time interval 220, FIG. 2A) in a superpixel readout mode of operation in order to capture regular probe images by reading out clusters of pixels, and in a single pixel readout mode of in order to capture normal images by reading out pixels individually. If the controller, consequently to using the pixel array in the superpixel mode, determines that an event of interest is indicated by one or more captured regular probe images, the controller may transition the pixel array from the superpixel readout mode to the single pixel readout mode and capture a normal image or a series of normal images for transmission, and, then, reuse the superpixel readout mode again and capture a subsequent regular probe image. If the controller, after using the pixel array in the superpixel mode, determines that there is no indication to an event of interest in the one or more captured regular probe images, the controller may reuse the superpixel readout mode and capture a subsequent regular probe image. The controller (e.g., controller 120) may be configured to perform any method that is disclosed herein.

While in some embodiments a specific controller is described as performing operations, in other embodiments other structures and other devices may be used.

In one embodiment an in-vivo device may include a sensor to sense a non-image parameter of the GI tract, and the controller may use the non-image parameter to corroborate an indicated event of interest. The in-vivo device may include a detector to detect content or bubble in the GI tract, and the controller may use the detector (and other sensory information; e.g., image data, motion sensor, localization data, etc.) to determine whether the in-vivo device is moving relative to the content or bubble, or the content or bubble is moving relative to the in-vivo device.

In one embodiment an in-vivo device may include an illumination source to illuminate the GI tract, and the controller may operate the illumination source in a first illumination mode (e.g., power save mode) when the pixel array is operated in the superpixel readout mode, and in a second illumination mode different than the first mode (e.g., full light mode or optimal light mode) when the pixel array is operated in the single pixel readout mode.

In one embodiment a controller may use the superpixel readout mode to capture a conditional probe image between two successive regular probe images if no normal image is to be captured between the two successive regular probe images. The controller may compare a currently captured conditional probe image with a past regular probe image(s) and/or with a past conditional probe image(s) and/or with a past normal image(s), and, based on the comparison result, the controller may determine whether an event of interest is indicated.

In one embodiment an in-vivo device may include a memory buffer and a transmitter, and the controller may store each captured normal image in the memory buffer and orderly transmit stored normal images to an external receiver according to a transmission queue.

Embodiments disclosed herein have many advantages over conventional in-vivo imaging systems. For example, some embodiments improve and upgrade the concept of adaptive frame rate ("AFR"). (In some in-vivo devices that use conventional AFR schemes the AFR scheme enables conditional selection between two predetermined frames per second ("FPS") rates; that is, a conventional in-vivo device can transition between two, predetermined, FPS rates, with one FPS rate being higher than the other. A problem with such AFR schemes is that images are captured and transmitted even though their transmission is not justified because, for example, they may bear no clinical information. Therefore, not only capturing and transmission of such images results in power and resources wasting, but it also, more often than not, results in using suboptimal FPS rate.

The methods and system disclosed herein provide for a new AFR scheme that avoids transmitting images, and thus wasting resources and battery power, whenever image transmission is unjustified clinically, and, at the same time, it provides an optimal FPS rate whenever transmission of images is justified, because applying the methods disclosed herein results in a 'post-factum' FPS rate that can change fast in real time between zero and a maximum value. (The value of the FPS rate subject of the present disclosure can be every $2^n$-based number (e.g., $2^n=1, 2, 4, 8, \ldots$) and up to 64 FPS, with 64 FPS being an example maximal value for FPS rate, and the FPS rate can change rapidly from any FPS value to any other FPS value within the zero-to-maximal range.) Therefore, the actual FPS rate obtained by using the AFR schemes disclosed herein better suits the real physical conditions that the in-vivo device is subjected to during a clinical (an imaging) procedure. (Better suits'—in terms of, for example, gained advantages: images that are ultimately transmitted are likely to include clinically important information; the number of images that an external system will receive and process will be significantly reduced; and battery power, as well as other on-board and remote/external resources, will be saved because only images that are worth transmitting (per the events of interest) will ultimately be captured and transmitted.)

In addition, the probe images are captured (but not transmitted) constantly at a maximal images per second rate, which enables the in-vivo device to respond (e.g., capture and transmit normal images) very quickly when the in-vivo device senses 'something' that is worth capturing and transmitting normal image(s) for. (As described herein, capturing and internally processing probe images in the in-vivo device is very frugal in terms of battery power and processing resources.)

A device, system and method in accordance with some embodiments of the invention may be used, for example, in conjunction with a device which may be swallowed. However, the scope of the present invention is not limited in this regard.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for an in-vivo device, the in-vivo device comprising a battery, a controller, a pixel array operable in a superpixel readout mode of operation to capture probe images by reading clusters of pixels, and in a single pixel readout mode of operation to capture normal images by reading pixels individually, the method comprising: causing by the controller, (i) operating the pixel array in the superpixel readout mode to capture a probe image and refraining from transmitting the probe image to save battery energy, wherein operating the pixel array in the superpixel readout mode comprises selecting a pixel binning scheme adapted to or optimized for an image parameter or image feature to be used for comparing probe images; (ii) in a case where at least one of the image parameter or the image feature related to the captured probe image(s) do not indicate an event of interest, repeating steps (i)-(ii); (iii) in a case where at least one of the image parameter or the image feature related to the captured probe image(s) indicate an event of interest, operating the pixel array in the single pixel readout mode and capturing and transmitting a normal image or a burst of normal images, and repeating steps (i)-(iii), wherein the superpixel readout mode includes clustering adjacent pixels in the pixel array to superpixels, and reading each particular superpixel of a cluster by reading one superpixel signal that represents an entire cluster of adjacent pixels of a particular superpixel; and further comprising calculating a score indicative of an event of interest for each probe image, and performing, for each currently captured probe image, (iv) in a case where the score of the currently captured probe image, individually or in comparison to scores of previously captured probe image, does not indicate an event of interest, capturing a subsequent probe image, refraining from transmitting the subsequent probe image and accessing the score for the subsequent probe image; and (v) in a case where the score of the currently captured probe image, individually or in comparison to scores of previously captured probe image, indicates an event of interest, capturing a normal image or a burst of normal images by operating the pixels in the single pixel readout mode, transmitting the normal image or the burst of normal images, capturing a subsequent probe image and repeating steps (iv)-(v); and (vi) calculating a difference score between the score of a currently captured probe image and the score of a previously captured probe image, wherein a score of each probe image equal to or greater than a first threshold and a difference score equal to or greater than a second threshold indicate an event of interest.

2. The method as in claim 1, wherein a number of normal images in the burst of normal images to be transmitted is determined according to the indicated event of interest.

3. The method as in claim 1, further comprising selecting a superpixel configuration according to an anticipated event of interest.

4. The method as in claim 1, further comprising sensing, by a sensor in the in-vivo device, a non-image parameter of a GI tract to corroborate an indicated event of interest, wherein the non-image parameter is selected from the group consisting of: acidity (pH), pressure and temperature.

5. The method as in claim 1, wherein the event of interest is selected from the group consisting of: movement of the in-vivo device relative to a scene imaged by the in-vivo device or relative to a landmark in a GI tract, a landmark in the GI tract, a particular location or segment in the GI tract, an organ of the GI tract, and a pathology.

6. The method as in claim 5, wherein the pathology is selected from the group consisting of polyp, ulcer, diverticulum, bleeding and Crohn's disease.

7. The method as in claim 1, wherein the score of a particular probe image is calculated based on any of an image parameter or an image feature detected in, related to or derived from the particular probe image, an imaging amplifier gain and an imaging light exposure time.

8. The method as in claim 1, wherein determining whether to capture and transmit a normal image or a burst of normal images comprises predicting movement of the in-vivo device.

9. The method as in claim 1, wherein a number of normal images in an image burst depends on any of: the location of the in-vivo device in the GI tract, a type of pathology captured by a probe image and a landmark detected in the GI tract.

* * * * *